US008207163B2

(12) United States Patent
Bhat et al.

(10) Patent No.: US 8,207,163 B2
(45) Date of Patent: Jun. 26, 2012

(54) COMPOSITIONS, SYNTHESIS, AND METHODS OF USING PIPERAZINE BASED ANTIPSYCHOTIC AGENTS

(75) Inventors: Laxminarayan Bhat, Cupertino, CA (US); Prabhu Prasad Mohapatra, San Jose, CA (US); Kouacou Adiey, San Jose, CA (US)

(73) Assignee: Reviva Pharmaceuticals, Inc., San Jose, CA (US)

( * ) Notice: Subject to any disclaimer, the term of this patent is extended or adjusted under 35 U.S.C. 154(b) by 291 days.

(21) Appl. No.: 12/473,079

(22) Filed: May 27, 2009

(65) Prior Publication Data

US 2009/0298819 A1    Dec. 3, 2009

Related U.S. Application Data

(60) Provisional application No. 61/056,183, filed on May 27, 2008.

(51) Int. Cl.
    A61K 31/495    (2006.01)
    A61K 31/538    (2006.01)
    C07D 265/36    (2006.01)
    C07D 241/04    (2006.01)
(52) U.S. Cl. .................................. 514/230.5; 544/105
(58) Field of Classification Search .................. 544/105; 514/230.5
    See application file for complete search history.

(56) References Cited

U.S. PATENT DOCUMENTS

| | | | |
|---|---|---|---|
| 3,770,734 | A | 11/1973 | Pesson et al. |
| 3,845,770 | A | 11/1974 | Theeuwes et al. |
| 3,916,899 | A | 11/1975 | Theeuwes et al. |
| 4,803,203 | A | 2/1989 | Caprathe et al. |
| 4,977,166 | A | 12/1990 | Hardy et al. |
| 5,112,598 | A | 5/1992 | Biesalski |
| 5,308,844 | A | 5/1994 | Rieu et al. |
| 5,556,611 | A | 9/1996 | Biesalski |
| 5,698,155 | A | 12/1997 | Grosswald et al. |
| 7,253,168 | B2 | 8/2007 | Hutchison et al. |

FOREIGN PATENT DOCUMENTS

| | | |
|---|---|---|
| EP | 0161498 A1 | 11/1985 |
| JP | 59070675 | 4/1984 |
| JP | 60 169467 A | 9/1985 |
| JP | 5 331151 A | 12/1993 |
| JP | 2007 137818 A | 6/2007 |
| WO | WO 03/064393 A1 | 8/2003 |
| WO | WO 2004/063162 A1 | 7/2004 |
| WO | WO 2004/099152 A1 | 11/2004 |
| WO | WO 2006/030446 A1 | 3/2006 |

OTHER PUBLICATIONS

European Extended Search Report, European Application No. 09767305.7, May 18, 2011, 7 pages.
European Supplementary Search Report, European Application No. 09767305.7, Jun. 6, 2011, 1 page.
Abernethy, D. R. et al., "Molecular Basis of Cardiovascular Drug Metabolism: Implications for Predicting Clinically Important Drug Interactions," Circulation 2000, pp. 1749-1753, vol. 101.
Bamba, M. et al., "Release Mechanisms in Gelforming Sustained Release Preparations," International Journal of Pharmaceutics, 1979, pp. 307-315, vol. 2.
Cheng, J. W. et al., "Updates on Cytochrome P450-Mediated Cardiovascular Drug Interactions," American Journal of Therapeutics, 2009, pp. 155-163, vol. 16.
Conley, R.R. et al., "Drug-Drug Interactions Associated with Second-Generation Antipsychotics: Considerations for Clinicians and Patients," Psychopharmacology Bulletin, 2007, pp. 77-97, vol. 40, No. 1.
Di Pietro, N.C. et al., "Dopamine and Serotonin Interactions in the Prefrontal Cortex: Isights on Antipsychotic Drugs and Their Mechanism of Action," Pharmacopsychiatry, 2007, pp. S27-S33, vol. 40, Suppl. 1.
During, M.J. et al., "Controlled Release of Dopamine from a Polymeric Brain Implant: In Vivo Characterization," Annals of Neurolology, Apr. 1989, pp. 351-356, vol. 25, No. 4.
Gundlach, A.L. et al., "$^{125}$I-Spiperone: A Novel Ligand for $D_2$ Dopamine Receptors," Life Sciences, 1984, pp. 1984-1988, vol. 35.
Howard, M.A. et al., "Intracerebral Drug Delivery in Rats with Lesion-Induced Memory Deficits," J. Neurosurg., 1989, pp. 105-112, vol. 71.
Hoyer, D. et al., "Molecular Pharmacology of 5-$HT_1$ and 5-$HT_2$ Recognition Sites in Rat and Pig Brain Membranes: Radioligand Binding Studies with [$^3$H]5-HT, [$^3$H]8-OH-DPAT, (−)[$^{125}$I]Iodocyanopindolol, [$^3$H]Mesulergine and [$^3$H]Ketanserin," European Journal of Pharmacology, 1985, pp. 13-23, vol. 118.
Jarvie, K.R. et al., "Molecular Cloning, Stable Expression and Desensitization of the Human Dopamine D1B / D5 Receptor," Journal of Receptor Research, 1993, pp. 573-590, vol. 13 No. 1-4.
Kalra, B. S., "Cytochrome P450 Enzymen Isoforms and Their Therapeutic Implications: An Update," Indian Journal of Medical Sciences, Feb. 2007, pp. 102-116, vol. 61, No. 2.
Langer, R. et al., "Chemical and Physical Structure of Polymers as Carriers for Controlled Release of Bioactive Agents: A Review," Journal of Macromolecular Science Reviews in Macromolecular Chemistry and Physics, 1983, pp. 61-126, vol. 23, No. 61. Langer, R., "New Methods of Drug Delivery," Science, Sep. 28, 1990, pp. 1527-1533, vol. 249.
Levy, R. et al., "Inhibition of Calcification of Bioprosthetic Heart Valves by Local Controlled-Release Diphosphonate," Science, Apr. 12, 1985, pp. 190-192, vol. 228, No. 4696.
Miyamoto, S. et al., "Treatments for Schizophrenia: A Critical Review of Pharmacology and Mechanisms of Action of Antipsychotic Drugs," Molecular Psychiatry, 2005, pp. 79-104, vol. 10.
Mulder, H. et al., "Prevalence of Patients Using Drugs Metabolized by Cytochrome P450 2D6 in Different Populations: a Cross-Sectional Study," The Annals of Pharmacotherapy, Mar. 2007, pp. 408-413, vol. 41, No. 3.
PCT International Search Report and Written Opinion, PCT Application No. PCT/US09/45320, Aug. 28, 2009, 7 pages.
Saudek, C.D. et al., "A Preliminary Trial of the Programmable Implantable Medication System for Insulation Delivery," The New England Journal of Medicine, Aug. 31, 1989, pp. 574-579, vol. 321, No. 9.
Schoeffter, P. et al., "How Selective is GR 43175? Interactions with Functional 5-$HT_{1A}$, 5-$HT_{1B}$, 5-$HT_{1C}$ and 5-$HT_{1D}$ Receptors," Naunyn-Schmiedeberg's Arch. Pharmac., 1989, pp. 135-138, vol. 340.

(Continued)

Primary Examiner — Kahsay T Habte
(74) Attorney, Agent, or Firm — Perkins Coie LLP.; Viola T. Kung

(57) ABSTRACT

The present invention provides novel piperazine derivatives which can be advantageously used for treating schizophrenia and related psychoses such as acute manic, bipolar disorder, autistic disorder and depression.

30 Claims, No Drawings

OTHER PUBLICATIONS

Sefton, M.V., "Implantable Pumps," Critical Reviews in Biomedical Engineering, 1987, pp. 201-240, vol. 14, Issue 3.

Snyder, S.H., "A Complex in Psychosis," Nature, Mar. 6, 2008, pp. 38-39, vol. 452, Issue No. 7183.

Stark, A.D. et al., "Interaction of the Novel Antipsychotic Aripiprazole with $5-HT_{1A}$ and $5-HT_{2A}$ Receptors: Functional Receptor-Binding and In Vivo Electrophysiological Studies," Psychopharmacology 2007, 190, pp. 373-382.

Verma, R.K. et al., "Osmotically Controlled Oral Drug Delivery," Drug Development and Industrial Pharmacy, 2000, pp. 695-708, vol. 26, No. 7.

Zhou, Q. et al., "Rational Prescription of Drugs Within Similar Therapeutic or Structural Class for Gastrointestinal Disease Treatment: Drug Metabolism and Its Related Interactions," World J. Gastroenterol, Nov. 14, 2007, pp. 5618-5628, vol. 13, No. 42.

Final Office Action Mailed Mar. 23, 2012 for U.S. Appl. No. 12/714,406.

Non-Final Office Action for U.S. Appl. No. 12/714,406, dated Jan. 27, 2012.

COMPOSITIONS, SYNTHESIS, AND METHODS OF USING PIPERAZINE BASED ANTIPSYCHOTIC AGENTS

CROSS-REFERENCE TO RELATED APPLICATIONS

This application claims priority from and benefit under 35 U.S.C. §119(e) of U.S. Provisional Patent Application No. 61/056,183, filed May 27, 2008, the disclosure of which is incorporated herein by reference.

FIELD OF THE INVENTION

The present invention relates to compositions of piperazine derivatives, synthesis of piperazine derivatives, and methods of using piperazine derivatives. The present invention more particularly relates to synthesis, compositions and methods of using piperazine based compounds which are useful for the pharmacological treatment of schizophrenia and related psychoses such as acute manic, bipolar disorder, autistic disorder and depression.

BACKGROUND OF THE INVENTION

Medications used to treat psychotic disorders are called antipsychotics. Typical antipsychotics (sometimes referred to as conventional antipsychotics) are class of first generation antipsychotic drugs and used to treat psychosis including schizophrenia. The typical antipsychotics include chlorpromazine (THORAZINE®), fluphenazine (PROLIXIN®), haloperidol (HALDOL®), thiothixene (NAVANE®), trifluoroperazine (STELAZINE®), perphenazine (TRILAFON®), and thioridazine (MELLARIL®). The second generation antipsychotics introduced in the 1990's are called atypical antipsychotics. Compared to the first generation antipsychotics, the atypical antipsychotics appear to be equally effective in reducing the positive symptoms like hallucinations and delusions but may be better than the typical antipsychotics at relieving the negative symptoms of schizophrenia such as apathy, withdrawal, emotional depression and the like. The atypical antipsychotics currently in clinical use include Aripiprazole (ABILIFY®), clozapine (CLOZARIL®), risperidone (RISPERDAL®), olanzapine (ZYPREXA®), quetiapine (SEROQUEL®), and ziprasidone (GEODON®).

Atypical antipsychotics have diminished propensity to cause extrapyramidal symptoms (EPS) and tardive dyskinesia (TD) than typical antipsychotics. Additional benefits associated with the atypical antipsychotics include better treatment of negative symptoms, better compliance, possible benefits for cognitive impairments, and lower rates of relapse. Within the class of atypical antipsychotics, however, differences exist both in efficacy and side effects. Clozapine does not cause EPS, and is clearly more effective than all other antipsychotics used in humans to date. It is however a life-altering drug, because of its side effects and need for continual medical monitoring, in some countries, for agranulocytosis. This has markedly limited its use. The other atypical antipsychotics with the greatest amount of efficacy data are risperidone and olanzapine. These drugs are the most commonly used first-line antipsychotics today. This is warranted because they are more clinically effective than conventional drugs and much easier to use than clozapine. However, both risperidone and olanzapine are limited by side effects. Risperidone causes prolactin elevations, dose-dependant EPS and some weight gain. Olanzapine use is associated with much more weight gain in addition to lipid and glucose abnormalities. Qetiapine and Ziprasidone may be safer alternatives to risperidone and olanzapine but these drugs do not appear to be as clinically effective as the other atypical antipsychotics. Aripiprazole is one of a new generation of atypical antipsychotic drugs approved by the FDA for the treatment of schizophrenia in November 2002 (Satyanarayana, C. et al. WO 2006/030446; Tsujimori, H. et al. WO 2004/063162; Salama, P. et al. WO 2004/099152; Wikstorm, H. et al. WO 2003/064393). It was approved for the treatment of acute mania and mixed episode associated with bipolar disorder in March 2005. Aripiprazole does not differ greatly from other atypical antipsychotics with respect to treatment response, efficacy and tolerability.

Atypical antipsychotics are increasingly being used in children and adolescents for a variety of psychiatric conditions. Conditions for which atypical antipsychotics are prescribed include bipolar disorder, psychotic depression, schizophrenia, pervasive developmental disorders, attention-deficit/hyperactivity disorder (ADHD), oppositional defiant disorder (ODD), and conduct disorder. They are also used symptomatically to treat rage, insomnia, and anorexia. Younger patients appear to be at a higher risk of adverse effects associated with the treatment of atypical antipsychotics especially weight gain and drug induced diabetes mellitus.

In general, atypical antipsychotics share many of the side effects of typical antipsychotics, including sedation, akathisia, weight gain, extrapyramidal symptoms (EPS), neuromalignant syndrome, and tardive dyskinesia; longer experience with them have shown that new risks need to be considered, such as metabolic syndromes and QTc prolongation. QTc prolongation is known to have potential liability to produce fatal cardiac arrhythmias of Torsades de Pointes (TdP). Drug induced adverse metabolic effects such as weight gain, lipid abnormalities, and diabetes mellitus have been identified as a major risk factor for various medical disorders that might be responsible for some of the increased morbidity and mortality rates in psychotic patients treated with atypical antipsychotics.

Off-target pharmacology and drug to drug interactions are mainly responsible for most of the adverse side effects associated with the atypical antipsychotics. All the atypical antipsychotic drugs currently being used for the treatment of schizophrenia and related psychotic disorders have poor therapeutic target selectivity. For example, one of the most widely prescribed atypical antipsychotic drugs, Olanzapine and the most effective atypical antipsychotic drug, clozapine are reported to have significant activities against more than 12 receptors such as dopamine ($D_1$, $D_2$, $D_3$ and $D_4$), serotonin (5-$HT_{2A}$, 5-$HT_{2C}$, 5-$HT_6$, and 5-$HT_7$), adrenergic (alpha 1 and alpha 2), histamine ($H_1$), muscarinic ($M_1$), Dopamine transporter (DAT) and norepinephrine transporter (NET) receptors (Miyamoto et al., Molecular Psychiatry, 2005, 10, 79). Similarly, the other FDA approved atypical antipsychotics such as risperidone and aripiprazole are also reported to have significant activities against more than nine of the receptors mentioned above. The current reasearch suggests that compounds exhibiting activity against dopamine ($D_2$) and serotonin (5-$HT_{1A}$ and 5-$HT_{2A}$) receptors may have the intended antipsychotic effect (Snyder, S. H., Nature 2008, 452, 38-39; Di Pietro, N. C., Seamans, J. K., Pharmacopsychitry 2007, 40(S1), S27-S33; Stark, A. D. et al., Psychopharmacology 2007, 190, 373-382) while compounds exhibiting activity against other receptors like serotonin, 5$HT_{2C}$, histamine ($H_1$), and adrenergic (alpha 1) may cause adverse side effects such as cardiac arrhythmias.

In addition to poor target selectivity, the most widely used atypical antipsychotics like aripiprazole, risperidone, olanzapine, quetiapine and clozapine are known to undergo cytochrome P450 (CYP 450) mediated hepatic metabolism in the body (Conley, R. R. and Kelly, D. L. Psychopharmacol Bull. 2007, 40(1), 77-97). Hepatic metabolism is also a key determinant of the potential for a given drug to be involved in clinically significant pharmacokinetic drug interactions (Cheng, J. W. et al., Am. J. Ther. 16(2), 155-163, 2009; Kalra, B. S., Indian J. Med. Sci. 61(1), 102-116, 2007; Zhou, Q. et al., World J. Gastroenterol 13(42), 5618-5628, 2007; Abernethy, D. R., Circulation 101, 1749-1753, 2000). Research suggests that aripiprazole is metabolized by CYP 450 isoenzymes 3A4 and 2D6, clozapine and Olanzapine are primarily metabolized by CYP1A2 and risperidone is metabolized by CYP 2D6. There are significant polymorphisms in patients for CYP isoenzymes and this polymorphism has been shown to substantially increase plasma levels of these atypical antipsychotics. For example, approximately 10% of the Caucasian population lacks CYP2D6 isoenzyme. Patients from the general hospital, geriatric patients, psychogeriatric patients and psychiatric patients are treated more frequently with at least one drug metabolized by CYP2D6 compared to patients in the general population. Approximately, 50% of psychiatric, psychogeriatric and geriatric patients take at least one drug metabolized by CYP2D6 for other than psychotic indication they have (Mulder H. et al. Ann Pharmacother. 2007, 41(3), 408-13). Thus, poor metabolizers, who lack particular CYP isoenzyme responsible for metabolizing atypical antipsychotic drugs, can be particularly predisposed to adverse drug interactions.

Although, the atypical antipsychotics (aripiprazole, clozapine, risperidone, olanzapine, quetiapine, and ziprasidone) currently in clinical use represent significant advances in treatment of people with schizophrenia, there is a need for new psychotropic drugs with improved safety profiles.

Therefore, development of a novel antipsychotics that preferably undergo significantly non-CYP mediated metabolism in the body and/or have improved therapeutic target selectivity than the currently available therapies would provide effective and safer medicines for the treatment of schizophrenia and related psychotic disorders.

SUMMARY OF THE INVENTION

The present invention provides compounds, synthesis of the compounds, compositions and methods of using the compounds for treating schizophrenia and related psychoses such as acute manic, bipolar disorder, autistic disorder and depression, where the compounds are piperazine derivatives. The present invention provides methods for synthesizing such piperazine compounds. The present invention also provides methods for using piperazine based atypical antipsychotics, and composition of piperazine based atypical antipsychotics for treating schizophrenia and related psychoses such as acute manic, bipolar disorder, autistic disorder and depression.

The compounds of the subject invention provide next generation novel antipsychotics that are particularly effective and safer for the treatment of schizophrenia. They are advantageous because of their highly desirable metabolic, pharmacokinetics and pharmacological profiles. The compounds of the invention are designed:

1) to exhibit affinity for dopamine $D_2$ receptor;
2) to exhibit affinity for serotonin 5-$HT_{1A}$ and 5-$HT_{2A}$ receptors;
3) to undergo significantly non-oxidative or non-CYP enzyme mediated metabolism in the human body;
4) to metabolize significantly by hydrolytic enzymes such as esterases and/or peptidases in the human body; and
5) to form therapeutically inactive or least active metabolite(s).

The features like non-cytochrome P450 enzymes mediated metabolism and therapeutically inactive or least active metabolites in the compounds of subject invention can mitigate the adverse side effects that are derived from cytochrome P450 mediated drug interactions. Therefore, having these features, the compounds of the inventions are more effective and safer for the treatment of schizophrenia in humans including patients who are on multiple medications for chronic diseases for example: chronic pain, diabetes, cardiovascular diseases, dementia, and asthma, and have poor functioning of liver and kidney.

In one aspect, the present invention provides piperazine derivatives comprising compounds of structural Formula (I):

Formula 1

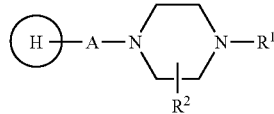

or a pharmaceutically acceptable salt, hydrate or solvate thereof provided that the compound comprises a soft moiety conjugated directly or via a spacer onto or inserted into one of the substituents $R^1$, $R^2$, and cyclic ring-H; wherein 'A' is selected to be —O—(CH$_2$)$_n$—, —S—(CH$_2$)$_n$—, —S(O)(O)—(CH$_2$)$_n$—, —NH—(CH$_2$)$_n$—, —CH$_2$—O—(CH$_2$)$_n$—, —(CH$_2$)$_n$—O—CH$_2$—CH$_2$—, —CH$_2$—S—(CH$_2$)$_n$—, —(CH$_2$)$_n$—S—CH$_2$—CH$_2$—, —CH$_2$—S(O)(O)—(CH$_2$)$_n$—, —(CH$_2$)$_n$—S(O)(O)—CH$_2$—CH$_2$—, —O—C(O)—(CH$_2$)$_n$—, —S—C(O)—(CH$_2$)$_n$—, —NH—C(O)—(CH$_2$)$_n$—, —CH$_2$—C(O)—O—(CH$_2$)$_n$—, —CH$_2$—C(O)—NH—(CH$_2$)$_n$—, —CH$_2$—C(O)—S—(CH$_2$)$_n$—, —(CH$_2$)$_n$—C(O)—O—CH$_2$—CH$_2$—, —(CH$_2$)$_n$—C(O)—NH—CH$_2$—CH$_2$—, —(CH$_2$)$_n$—C(O)—S—CH$_2$—CH$_2$—, —CH$_2$—O—C(O)—(CH$_2$)$_n$—, —CH$_2$—NH—C(O)—(CH$_2$)$_n$—, —CH$_2$—S—C(O)—(CH$_2$)$_n$—, —(CH$_2$)$_n$—O—C(O)—CH$_2$—CH$_2$—, (CH$_2$)$_n$—NH—C(O)—CH$_2$—CH$_2$—, or (CH$_2$)$_n$—S—C(O)—CH$_2$—CH$_2$—, wherein n is an integer from 1 to 7;

cyclic ring-'H' is selected to be

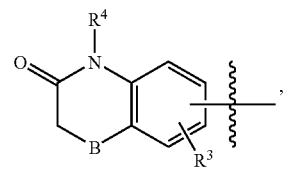,

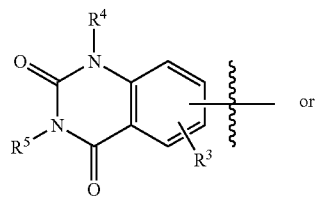 or

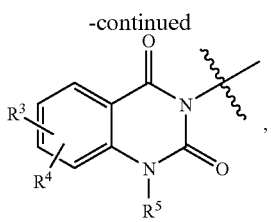

wherein 'B' is O, S, S(O)(O), or NR$^5$;

$R^1, R^2, R^3, R^4$, and $R^5$ are independently selected to be hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl, acylalkyloxycarbonyl, acyloxyalkyloxycarbonyl, acylalkyloxycarbonylamino, acyloxyalkyloxycarbonylamino, alkoxy, alkoxycarbonyl, alkoxycarbonylalkoxy, alkoxycarbonyllalkylamino, alkylasulfinyl, alkylsulfonyl, alkylthio, amino, alkylamino, arylalkylamino, dialkkylamino, arylalkoxy, arylalkoxycarbonylalkoxy, arylalkoxycarbonylalkylamino, aryloxycarbonyl, aryloxycarbonylalkoxy, aryloxycarbonylalkylamino, carboxy, carbamoyl, carbamate, carbonate, cyano, halo, heteroaryloxycarbonyl, hydroxy, phosphate, phosphonate, sulfate, sulfonate, or sulfonamide; optionally $R^1$ and $R^2$ can together form a 5- or 6-membered ring which may contain one or more heteroatoms selected from O, N, or S and that ring may be optionally substituted with substituents selected from alkyl, substituted alkyl, halo, hydroxyl, and carbonyl; optionally $R^1, R^2, R^3, R^4, R^5$ and A may substituted with isotopes that include, but not limited to $^2$H (deuterium), $^3$H (tritium), $^{13}$C, $^{15}$N, $^{18}$O, $^{17}$O, $^{31}$P, $^{32}$P, $^{35}$S, $^{18}$F and $^{36}$Cl.

The soft moiety can be an amide, an ester, a carbonate, a phosphate, a sulfate, or a carbamate. In one aspect of the invention, the soft-moiety further comprises a spacer. The spacer can be O, S, alkyl, substituted alkyl, acyl, acylamino, alkoxy, alkylamino, alkylthio, amino, carboxy, or alkoxycarbonyl.

DETAILED DESCRIPTION OF THE INVENTION

The present invention relates to synthesis, compositions and methods of using piperazine derivatives which are useful for treating schizophrenia and related psychoses such as acute manic, bipolar disorder, autistic disorder and depression. The present invention provides compounds, compositions and methods for pharmacological treatment of schizophrenia and related psychoses such as acute manic, bipolar disorder, autistic disorder, and depression.

Definitions

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Definition of standard chemistry terms may be found in reference works, including Carey and Sundberg (1992) "Advanced Organic Chemistry 3$^{rd}$ Ed." Vols. A and B, Plenum Press, N.Y. The practice of the present invention will employ, unless otherwise indicated, conventional methods of mass spectroscopy, protein chemistry, biochemistry, recombinant DNA techniques and pharmacology, within the skill of the art. The compositions and formulations described herein can be practiced employing the pharmaceutically acceptable excipients and salts available in *Remington's Pharmaceutical Sciences*, 18$^{th}$ Edition (Easton, Pa.: Mack Publishing Company, 1990).

"Compounds of the invention" refers to compounds encompassed by structural Formulae (I)-(XI) disclosed herein. The compounds of the invention can be identified either by their chemical structure and/or chemical name. When the chemical structure and chemical name conflict, the chemical structures is determinative of the identity of the compound. The compounds of the invention may contain one or more chiral centers and/or double bonds and therefore, may exist as stereoisomers, such as double-bond isomers (i.e., geometric isomers), enantiomers or diastereoisomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds of the invention may also exist in several tautomeric forms including the enol form, the keto form and mixtures thereof. Accordingly, the chemical structures depicted herein encompass all possible tautomeric forms of the illustrated compounds. The compounds of the invention also include isotopically labeled compounds where one or more atoms have an atomic mass different from the atomic mass of conventionally found in nature. Examples of isotopes that may be incorporated into the compounds of the invention include, but are not limited to $^2$H, $^3$H, $^{13}$C, $^{15}$N, $^{18}$O, $^{17}$O, $^{31}$P, $^{32}$P, $^{35}$S, $^{18}$F and $^{36}$Cl. Further, it should be understood, when partial structures of the compounds of the invention are illustrated, that brackets of dashes indicate the point of attachment of the partial structure to the rest of the molecule.

"Composition of the invention" refers to at least one compound of the invention and a pharmaceutically acceptable vehicle, with which the compound is administered to a patient. When administered to a patient, the compounds of the invention are administered is isolated form, which means separated from a synthetic organic reaction mixture.

"Alkyl" refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to methyl; ethyls such as ethanyl, ethenyl, ethynyl; propyls such as propan-1-yl, propan-2yl, cyclopropan-1-yl, prop-1-en-1-yl, prop-1-en-2-yl, prop-2-en-1-yl (allyl), cycloprop-1-en-1yl, cycloprop-2-en-1yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

The term "alkyl" specifically intended to include radicals having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl," are used. Preferably, an alkyl group comprises from 1-20 carbon atoms, more preferably, from 1 to 10 carbon atoms.

"Alkanyl" refers to a saturated branched, straight-chain or cyclic alkyl radical derived by the removal of one hydrogen atom from a single carbon atom of a parent alkane. Typical alkanyl groups include but are not limited to , methanyl; ethanyl; propanyls such as propan-1-yl, propan-2-yl(isopropyl), cyclopropan-1-yl, etc.; butanyls such as butan-1-yl, butan-2-yl(sec-butyl), 2-methyl-propan-1-yl(isobutyl), 2-methyl-propan-2-yl(t-butyl), cyclobutan-1-yl, etc.; and the like.

"Alkenyl" refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl(allyl), prop-2-en-2-yl, cycloprop-1-en-1-yl, cycloprop-2-en-1-yl; butenyls such as but-1-en-1-yl, but-1-en-2-yl, 2-methy-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien 1-yl, etc.; and the like.

"Alkynyl" refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn3-yl, but-3-yn-1-yl, etc.; and the like.

"Acyl" refers to a radical —C(O)R, where R is hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to formyl, acetyl, cyclohexylcarbonyl, cyclohexylmethylcarbonyl, benzoyl, benzylcarbonyl and the like.

"Acyloxyalkyloxycarbonyl" refers to a radical —C(O)OCR'R"OC(O)R'", where R', R", and R'" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but not limited to —C(O)OCH$_2$OC(O)CH$_3$, —C(O)OCH$_2$OC(O)CH$_2$CH$_3$, —C(O)OCH(CH$_3$)OC(O)CH$_2$CH$_3$, —C(O)OCH(CH$_3$)OC(O)C$_6$H$_5$ and the like.

"Acylalkyloxycarbonyl" refers to a radical —C(O)OCR'R"C(O)R'", where R', R", and R'" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but not limited to —C(O)OCH$_2$C(O)CH$_3$, —C(O)OCH$_2$C(O)CH$_2$CH$_3$, —C(O)OCH(CH$_3$)C(O)CH$_2$CH$_3$, —C(O)OCH(CH$_3$)C(O)C$_6$H$_5$ and the like.

"Acyloxyalkyloxycarbonylamino" refers to a radical —NRC(O)OCR'R"OC(O)R'", where R, R', R", and R'" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but not limited to —NHC(O)OCH$_2$OC(O)CH$_3$, —NHC(O)OCH$_2$OC(O)CH$_2$CH$_3$, —NHC(O)OCH(CH$_3$)OC(O)CH$_2$CH$_3$, —NHC(O)OCH(CH$_3$)OC(O)C$_6$H$_5$ and the like.

"Acylalkyloxycarbonylamino" refers to a radical —NRC(O)OCR'R"C(O)R'", where R, R', R", and R'" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but not limited to —NHC(O)OCH$_2$C(O)CH$_3$, —NHC(O)OCH$_2$C(O)CH$_2$CH$_3$, —NHC(O)OCH(CH$_3$)C(O)CH$_2$CH$_3$, —NHC(O)OCH(CH$_3$)C(O)C$_6$H$_5$ and the like.

"Acylamino" refers to "Amide" as defined herein.

"Alkylamino" means a radical —NHR where R represents an alkyl, or cycloalkyl group as defined herein that may be optionally substituted by one or more substituents as defined herein. Representative examples include, but are not limited to, methylamino, ethylamino, 1-methylethylamino, cyclohexylamino and the like.

"Alkoxy" refers to a radical —OR where R represents an alkyl, or cycloalkyl group as defined herein that may be optionally substituted by one or more substituents as defined herein. Representative examples include, but are not limited to methoxy, ethoxy, propoxy, butoxy, cyclohexyloxy and the like.

"Alkoxycarbonyl" refers to a radical —C(O)-alkoxy where alkoxy is as defined herein.

"Alkoxycarbonylalkoxy" refers to a radical —OCR'R"C(O)-alkoxy where alkoxy is as defined herein. Similarly, where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to —OCH$_2$C(O)OCH$_3$, —OCH$_2$C(O)OCH$_2$CH$_3$, —OCH(CH$_3$)C(O)OCH$_2$CH$_3$, —OCH(C$_6$H$_5$)C(O)OCH$_2$CH$_3$, —OCH(CH$_2$C$_6$H$_5$)C(O)OCH$_2$CH$_3$, —OC(CH$_3$)(CH$_3$)C(O)OCH$_2$CH$_3$, and the like.

"Alkoxycarbonylalkylamino" refers to a radical —NRCR'R"C(O)-alkoxy where alkoxy is as defined herein. Similarly, where R, R', R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to —NHCH$_2$C(O)OCH$_3$, —N(CH$_3$)CH$_2$C(O)OCH$_2$CH$_3$, —NHCH(CH$_3$)C(O)OCH$_2$CH$_3$, —NHCH(C$_6$H$_5$)C(O)OCH$_2$CH$_3$, —NHCH(CH$_2$C$_6$H$_5$)C(O)OCH$_2$CH$_3$, —NHC(CH$_3$)(CH$_3$)C(O)OCH$_2$CH$_3$, and the like.

"Alkylsulfonyl" refers to a radical —S(O)$_2$R where R is an alkyl, or cycloalkyl group as defined herein that may be optionally substituted by one or more substituents as defined herein. Representative examples include, but are not limited to, methylsulfonyl, ethylsulfonyl, propylsulfonyl, butylsulfonyl, and the like.

"Alkylsulfinyl" refers to a radical —S(O)R where R is an alkyl, or cycloalkyl group as defined herein that may be optionally substituted by one or more substituents as defined herein. Representative examples include, but are not limited to, methylsulfinyl, ethylsulfinyl, propylsulfinyl, butylsulfinyl, and the like.

"Alkylthio" refers to a radical —SR where R is an alkyl or cycloalkyl group as defined herein that may be optionally substituted by one or more substituents as defined herein. Representative examples include, but are not limited to methylthio, ethylthio, propylthio, butylthio, and the like.

"Amide or Acylamino" refers to a radical —NR'C(O)R", where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

Representative examples include, but are not limited to, formylamino acetylamino, cyclohexylcarbonylamino, cyclohexylmethylcarbonyl-amino, benzoylamino, benzylcarbonylamino and the like.

"Amino" refers to the radical —$NH_2$

"Aryl" refers to a monovalent aromatic hydrocarbon radical derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorine, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleidene, pyrene, pyranthrene, rubicene, triphenylene, trinaphthalene, and the like. Preferable, an aryl group comprises from 6 to 20 carbon atoms, more preferably, between 6 to 12 carbon atoms.

"Arylalkyl" refers to an acyclic alkyl in which one of the hydrogen atoms bonded to a carbon atom, typically a terminal or sp$^3$ carbon atom, is replaced with an aryl group. Typically arylalkyl groups include, but not limited to, benzyl, 2-phenylethan-1-yl, 2-phenylethen-1-yl, naphthylmethyl, 2-naphthylethan-1-yl, 2-naphthylethene-1-yl, naphthobenzyl, 2-naphthophenylethan-1-yl and the like. Where specific alkyl moieties are intended, the nomenclature arylalkany, arylalkenyl and/or arylalkynyl is used. Preferably, an arylalkyl group is ($C_6$-$C_{30}$)arylalkyl, e.g., the alkanyl, alkenyl or alkynyl moiety of the arylalkyl group is ($C_1$-$C_{10}$) and the aryl moiety is ($C_6$-$C_{20}$), more preferably, an arylalkyl group is ($C_6$-$C_{20}$) arylalkyl, e.g., the alkanyl, alkenyl or alkynyl moiety of the arylalkyl group is ($C_1$-$C_8$) and the aryl moiety is ($C_6$-$C_{12}$).

"Arylalkoxy" refers to an —O-arylalkyl radical where arylalkyl is as defined herein that may be optionally substituted by one or more substituents as defined herein.

"Arylalkoxycarbonylalkoxy" refers to a radical —OCR'R"C(O)-arylalkoxy where arylalkoxy is as defined herein. Similarly, where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to —$OCH_2C(O)OCH_2C_6H_5$, —$OCH(CH_3)C(O)OCH_2C_6H_5$, —$OCH(C_6H_5)C(O)O$ $CH_2C_6H_5$, —$OCH(CH_2C_6H_5)C(O)OCH_2C_6H_5$, —$OC(CH_3)(CH_3)C(O)OCH_2C_6H_5$, and the like.

"Arylalkoxycarbonylalkylamino" refers to a radical —NRCR'R"C(O)-arylalkoxy where arylalkoxy is as defined herein. Similarly, where R, R', R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to —$NHCH_2C(O)OCH_2C_6H_5$, —$N(CH_3)CH_2C(O)OCH_2C_6H_5$, —$NHCH(CH_3)C(O)OCH_2C_6H_5$, —$NHCH(C_6H_5)C(O)OCH_2C_6H_5$, —$NHCH(CH_2C_6H_5)C(O)OCH_2C_6H_5$, —$NHC(CH_3)(CH_3)C(O)OCH_2C_6H_5$, and the like.

"Aryloxycarbonyl" refers to radical —C(O)—O-aryl where aryl is defined herein that may be optionally substituted by one or more substituents as defined herein.

"Aryloxycarbonylalkoxy" refers to a radical —OCR'R"C(O)-aryloxy where aryloxy is as defined herein. Similarly, where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to —$OCH_2C(O)OC_6H_5$, —$OCH(CH_3)C(O)OC_6H_5$, —$OCH(C_6H_5)C(O)OC_6H_5$, —$OCH(CH_2C_6H_5)C(O)OC_6H_5$, —$OC(CH_3)(CH_3)C(O)OC_6H_5$, and the like.

"Aryloxycarbonylalkylamino" refers to a radical —NRCR'R"C(O)-aryloxy where aryloxy is as defined herein. Similarly, where R, R', R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to —$NHCH_2C(O)OC_6H_5$, —$N(CH_3)CH_2C(O)OC_6H_5$, —$NHCH(CH_3)C(O)OC_6H_5$, —$NHCH(C_6H_5)C(O)OC_6H_5$, —$NHCH(CH_2C_6H_5)C(O)OC_6H_5$, —$NHC(CH_3)(CH_3)C(O)OC_6H_5$, and the like.

"Carbamoyl" refers to the radical —C(O)NRR where each R group is independently, hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Carbamate" refers to a radical —NR'C(O)OR", where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to, methylcarbamate (—$NHC(O)OCH_3$), ethylcarbamate (—$NHC(O)OCH_2CH_3$), benzylcarbamate (—$NHC(O)OCH_2C_6H_5$), and the like.

"Carbonate" refers to a radical —OC(O)OR, where R is alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to, methyl carbonate (—$C(O)OCH_3$), cyclohexyl carbonate (—$C(O)OC_6H_{11}$), phenyl carbonate (—$C(O)OC_6H_5$), benzyl carbonate (—$C(O)OCH_2C_6H_5$), and the like.

"Carboxy" means the radical —C(O)OH.

"Cyano" means the radical —CN.

"Cycloalkyl" refers to a substituted or unsubstituted cylic alkyl radical. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. In a preferred embodiment, the cycloalkyl group is ($C_3$-$C_{10}$) cycloalkyl, more preferably ($C_3$-$C_7$) cycloalkyl.

"Cycloheteroalkyl" refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, imidazolidine, morpholine, piperazine, piperidine, pyrazolidine, pyrrolidine, quinuclidine, and the like.

"Cycloheteroalkoxycarbonyl" refers to a radical —C(O)—OR where R is cycloheteroalkyl as defined herein that may be optionally substituted by one or more substituents as defined herein.

"Dialkylamino" means a radical —NRR' where R and R' independently represent an alkyl or cycloalkyl group as defined herein that may be optionally substituted by one or more substituents as defined herein. Representative examples include, but are not limited to dimethylamino, methylethylamino, di-(1-methylethyl)amino, (cyclohexyl)(methyl)amino, (cyclohexyl)(ethyl)amino, (cyclohexyl)(propyl)amino, and the like.

"Derived from a drug" refers to a fragment that is structurally related to such a drug. The structure of the fragment is identical to the drug except where a hydrogen atom attached to a heteroatom (N or O) has been replaced with a covalent bond to another group (typically, a promoiety). Note that when a drug is a salt form of a carboxylic, phosphonic or phosphoric acid, the corresponding structural fragment derived from such a drug is considered to be derived from the protonated acid form.

"Drug" refers to a compound that exhibits therapeutic and/or prophylactic and/or diagnostic utility when administered in effective amounts to a patient or a mammal.

"Ester" refers to a radical —C(O)OR, where R is alkyl, substituted alkyl, cycloalkyl, substituted cycloalkyl, cycloheteroalkyl, substituted cycloheteroalkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl as defined herein that may be optionally substituted by one or more substituents as defined herein. Representative examples include, but are not limited to, methyl ester (—C(O)OCH$_3$), cyclohexyl ester (—C(O)OC$_6$H$_{11}$), phenyl ester (—C(O)OC$_6$H$_5$), benzyl ester (—C(O)OCH$_2$C$_6$H$_5$), and the like.

"Ether" refers to a radical —OR, where R is alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Halo" means fluoro, chloro, bromo, or iodo.

"Heteroalkoxy" means an —O-heteroalkyl radical where heteroalkyl is as defined herein that may be optionally substituted by one or more substituents as defined herein.

"Heteroalkyl, Heteroalkanyl, Heteroalkenyl, Heteroalkynyl" refer to alkyl, alkanyl, alkenyl and alkynyl groups, respectively, in which one or more of the carbon atoms (and any associated hydrogen atoms) are each independently replaced with the same or different heteroatomic groups. Typical heteroatomic groups include, but are not limited to —O—, —S—, —O—O—, —S—S—, —OS—, —NR', =N—N=, —N=N—, —N=N—NR'—, —PH—, —P(O)$_2$—, —O—P(O)—, —S(O)—, —S(O)$_2$—, —SnH$_2$—, and the like, wherein R' is hydrogen, alkyl, substituted alkyl, cycloalkyl, substituted cycloalkyl, aryl or substituted aryl that may be optionally substituted by one or more substituents as defined herein.

"Heteroaryl" refers to a monovalent heteroaromatic radical derived by the removal of one hydrogen atom from a single atom of a parent heteroaromatic ring system. Typical heteroaryl groups include, but are not limited to, groups derived from acridine, arsindole, carbazole, carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is between 5-20 membered heteroaryl, with 5-10 membered heteroaryl being particularly preferred. Preferred heteroaryl groups are those derived from thiophene, pyrrole, benzothiophene, benzofuran, indole, pyridine, quinoline, imidazole, oxazole and pyrazine.

"Heteroaryloxycarbonyl" refers to a radical —C(O)—OR where R is heteroaryl as defined that may be optionally substituted by one or more substituents as defined herein.

"Heteroarylalkyl" refers to an acyclic alkyl radical in which one of the hydrogen atoms bonded to a carbon atom, typically a terminal or sp3 carbon atom, is replaced with a heteroaryl group. Where specific alkyl moieties are intended, the nomenclature heteroarylalkanyl, heteroarylalkenyl and/or heteroarylalkynyl is used. Preferably, the heteroarylalkyl radical is a 6-30 carbon membered heteroarylalkyl, e.g., the alkanyl, alkenyl or alkynyl moiety of the heteroarylalkyl is 1-10 membered and the heteroaryl moiety is a 5-20 membered heteroaryl, more preferably, a 6-20 membered heteroarylalkyl, e.g., the alkanyl, alkenyl or alkynyl moiety of the heteroarylalkyl is 1-8 membered and the heteroaryl moiety is a 5-12 membered heteroaryl.

"Hydroxy" means the radical —OH.

"Oxo" means the divalent radical =O.

As used herein, the term "patient" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. The term does not denote a particular age or gender.

"Pharmaceutically acceptable" means approved or approvable by a regulatory agency of the Federal or state government or listed in the U.S. Pharmacopoeia or other generally recognized pharmacopoeia for use in animals, and more particularly in humans.

"Pharmaceutically acceptable salt" refers to a salt of a compound of the invention, which is pharmaceutically acceptable and possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentane propionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2,2,2]-oct-2-ene-1-carboxylic acid, glucoheptonic acid, 3-phenylpropionic acid, trimethylacetic acid, tertiary butylacetic acid, laurylsulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Pharmaceutically acceptable vehicle" refers to a diluent, adjuvant, excipient or carrier with which a compound of the invention is administered.

"Phosphate" refers to a radical —OP(O)(OR')(OR"), where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Phosphonate" refers to a radical —P(O)(OR')(OR"), where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Preventing" or "Prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease).

"Prodrug" refers to a derivative of a drug molecule that requires a transformation within the body to release the active drug. Prodrugs are frequently (though not necessarily) pharmacologically inactive until converted to the parent drug.

"Promoiety" refers to a form of protecting group that when used to mask a functional group within a drug molecule converts the drug into a prodrug. Typically, the promoiety will be attached to the drug via bond(s) that are cleaved by enzymatic or non-enzymatic means in vivo.

"Protecting group" refers to a group of atoms that when attached to a reactive group in a molecule masks, reduces or prevents that reactivity. Examples of protecting groups can be found in Green et al., "Protective Groups in Organic Chemistry", (Wiley, $2^{nd}$ ed. 1991) and Harrison et al., "Compendium of Synthetic Organic Methods", vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilylethanesulfonyl ("SES"), trityl and substituted trityl groups, allyloxycarbonyl, 9-fluorenylmethyloxy-carbonyl ("FMOC"), nitroveratryloxycarbonyl ("NVOC") and the like. Representative hydroxyl protecting groups include, but are not limited to, those where the hydroxyl group is either acylated or alkylated such as benzyl, and trialkylsilyl ethers and allyl ethers.

"Racemate" refers to an equimolar mixture of enantiomers of a chiral molecule.

"Soft moiety" refers to a moiety that contain hydrolysable bonds that can be incorporated into compounds according to the invention include but not limited are amide (—NHC(O)—), ester (—C(O)O—), carbonate (—OC(O)O—), phosphate(—OP(O)O—), sulfate (—OS(O)(O)O—), carbamate or urethane (—NHC(O)O—), glycoside or other bonds that can be cleaved by hydrolases. A glycoside moiety is formed by the conjugation of a sugar group through its anomeric carbon to another group via oxygen (as an O-glycosidic bond) or sulfur (as a S-glycosidic bond).

"Spacer" refers to a alkyl, aryl, arylalkyl, heteroalkyl and heteroaryl group which is optionally substituted by acylalkyloxycarbonyl, acyloxyalkyloxycarbonyl, acylalkyloxycarbonylamino, acyloxyalkyloxycarbonylamino, alkoxy, alkoxycarbonyl, alkoxycarbonylalkoxy, alkoxycarbonyllalkylamino, alkylasulfinyl, alkylsulfonyl, alkylthio, amino, alkylamino, arylalkylamino, dialkkylamino, arylalkoxy, arylalkoxycarbonylalkoxy, arylalkoxycarbonylalkylamino, aryloxycarbonyl, arylloxycarbonylalkoxy, aryloxycarbonylalkylamino, carboxy, carbamoyl, carbamate, carbonate, cyano, halo, heteroaryloxycarbonyl, hydroxy, phosphate, phosphonate, sulfate, sulfonate, sulfonamide and/or, in case of alkyl, optionally interrupted by one or more of O, S and N($R^{51}$). $R^{51}$ can be H, lower alkyl, and substituted lower alkyl.

"Substituted" refers to a group in which one or more hydrogen atoms are each independently replaced with the same or different substituents(s). Typical substituents include, but are not limited to, —X, —$R^{54}$, —$O^-$, =O, —$OR^{54}$, —$SR^{54}$, —S, =S, —$NR^{54}R^{55}$, =$NR^{54}$, —$CX_3$, —$CF_3$, —CN, —OCN, —SCN, —NO, —$NO_2$, =$N_2$, —$N_3$, —$S(O)_2O^-$, —$S(O)_2$OH, —$S(O)_2R^{54}$, —$OS(O)_2O^{31}$, —$OS(O)_2R^{54}$, —P(O)(O—)$_2$, —$P(O)(OR^{14})(O^{31})$, —$OP(O)(OR^{54})(OR^{55})$, —$C(O)R^{54}$, —$C(S)R^{54}$, —$C(O)OR^{54}$, —$C(O)NR^{54}R^{55}$, —$C(O)O^-$, —$C(S)OR^{54}$, —$NR^{56}C(O)NR^{54}R^{55}$, —$NR^{56}C(S)NR^{54}R^{55}$, —$NR^{57}C(NR^{56})NR^{54}R^{55}$ and —$C(NR^{56})NR^{54}R^{55}$, where each X is independently a halogen; each $R^{54}$, $R^{55}$, $R^{56}$ and $R^{57}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl, —$NR^{58}R^{59}$, —$C(O)R^{58}$ or —$S(O)_2R^{58}$ or optionally $R^{58}$ and $R^{59}$ together with the atom to which they are both attached form a cycloheteroalkyl or substituted cycloheteroalkyl ring; and $R^{58}$ and $R^{59}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl.

"Sulfate" refers to a radical —OS(O)(O)OR, where R is hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Sulfonamide" refers to a radical —S(O)(O)NR'R", where R' and R" are independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein or optionally R' and R" together with the atom to which they are both attached form a cycloheteroalkyl or substituted cycloheteroalkyl ring. Representative examples include but not limited to azetidinyl, pyrrolidinyl, piperidinyl, morpholinyl, 4-(NR'")-piperazinyl or imidazolyl group wherein said group may be optionally substituted by one or more substituents as defined herein. R'" hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Sulfonate" refers to a radical —S(O)(O)OR, where R is hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Thio" means the radical —SH.

"Thio ether" refers to a radical —SR, where R is alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Treating" or "Treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the patient. In yet another embodiment, "treating" or "treatment" refers to inhibiting the disease or disorder, either physically (e.g., stabilization of a discernible symptom), physiologically, (e.g., stabilization of a physical parameter), or both. In yet another embodiment, "treating" or "treatment" refers to delaying the onset of the disease or disorder.

"Therapeutically effective amount" means the amount of a compound that, when administered to a patient for treating a disease, is sufficient to effect such treatment for the disease.

The "therapeutically effective amount" will vary depending on the compound, the disease and is severity and the age, weight, etc., of the patient to be treated, and can be determined by one of skill in the art without undue experimentation.

Reference now will be made in detail to preferred embodiments of the invention. While the invention will be described in conjunction with preferred embodiments, it will be understood that it is not intended to limit the invention to those preferred embodiments. To the contrary, it is intended to cover alternatives, modifications, and equivalents as may be included within the spirit and scope of the invention as defined by the appended claims.

Compounds of the Invention

The present invention provides piperazine based antipsychotic agents comprising compounds of structural Formula (I):

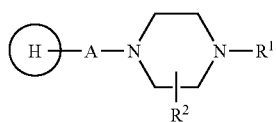

Formula 1 or a pharmaceutically acceptable salt, hydrate or solvate thereof provided that the compounds of the invention comprise a soft moiety conjugated directly or via a spacer onto or inserted into one of the substituents $R^1$, $R^2$, and cyclic ring-H; wherein 'A' is selected to be —O—$(CH_2)_n$—, —S—$(CH_2)_n$—, —S(O)(O)—$(CH_2)_n$—, —NH—$(CH_2)_n$—, —$CH_2$—O—$(CH_2)_n$—, —$(CH_2)_n$—O—$CH_2$—$CH_2$—, —$CH_2$—S—$(CH_2)_n$—, —$(CH_2)_n$—S—$CH_2$—$CH_2$—, —$CH_2$—S(O)(O)—$(CH_2)_n$—, —$(CH_2)_n$—S(O)(O)—$CH_2$—$CH_2$—, —O—C(O)—$(CH_2)_n$—, —S—C(O)—$(CH_2)_n$—, —NH—C(O)—$(CH_2)_n$—, —$CH_2$—C(O)—O—$(CH_2)_n$—, —$CH_2$—C(O)—NH—$(CH_2)_n$—, —$CH_2$—C(O)—S—$(CH_2)_n$—, —$(CH_2)_n$—C(O)—O—$CH_2$—$CH_2$—, —$(CH_2)_n$—C(O)—NH—$CH_2$—$CH_2$—, —$(CH_2)_n$—C(O)—S—$CH_2$—$CH_2$—, —$CH_2$—O—C(O)—$(CH_2)_n$—, —$CH_2$—NH—C(O)—$(CH_2)_n$—, —$CH_2$—S—C(O)—$(CH_2)_n$—, —$(CH_2)_n$—O—C(O)—$CH_2$—$CH_2$—, $(CH_2)_n$—NH—C(O)—$CH_2$—$CH_2$—, or $(CH_2)_n$—S—C(O)—$CH_2$—$CH_2$—, wherein n is an integer from 1 to 7;

cyclic ring-'H' is selected to be

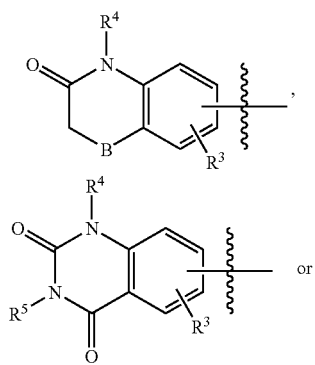

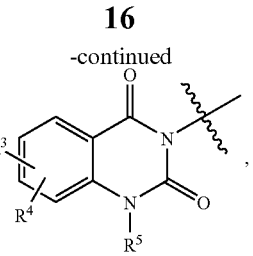

wherein 'B' is O, S, S(O)(O), or $NR^5$;

$R^1$, $R^2$, $R^3$, $R^4$, and $R^5$ are independently selected to be hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl, acylalkyloxycarbonyl, acyloxyalkyloxycarbonyl, acylalkyloxycarbonylamino, acyloxyalkyloxycarbonylamino, alkoxy, alkoxycarbonyl, alkoxycarbonylalkoxy, alkoxycarbonyllalkylamino, alkylasulfinyl, alkylsulfonyl, alkylthio, amino, alkylamino, arylalkylamino, dialkkylamino, arylalkoxy, arylalkoxycarbonylalkoxy, arylalkoxycarbonylalkylamino, aryloxycarbonyl, arylloxycarbonylalkoxy, aryloxycarbonylalkylamino, carboxy, carbamoyl, carbamate, carbonate, cyano, halo, heteroaryloxycarbonyl, hydroxy, phosphate, phosphonate, sulfate, sulfonate, or sulfonamide; optionally $R^1$ and $R^2$ can together form a 5- or 6-membered ring which may contain one or more heteroatoms selected from O, N, or S and that ring may be optionally substituted with substituents selected from alkyl, substituted alkyl, halo, hydroxyl, and carbonyl; optionally $R^1$, $R^2$, $R^3$, $R^4$, $R^5$ and A may substituted with isotopes that include, but not limited to $^2H$ (deuterium), $^3H$ (tritium), $^{13}C$, $^{15}N$, $^{18}O$, $^{17}O$, $^{31}P$, $^{32}P$, $^{35}S$, $^{18}F$ and $^{36}Cl$.

In one aspect of the invention, compounds of structural Formula (II) are described:

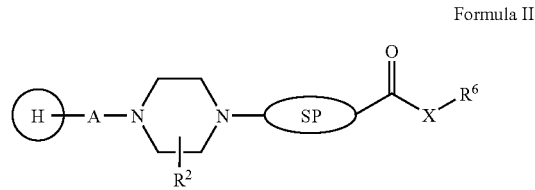

Formula II or a pharmaceutically acceptable salt, hydrate or solvate thereof, wherein X can be O, S, NH or $NR^7$;

SP is a spacer;

'A' is selected to be —O—$(CH_2)_n$—, —S—$(CH_2)_n$—, —S(O)(O)—$(CH_2)_n$—, —NH—$(CH_2)_n$—, —$CH_2$—O—$(CH_2)_n$—, —$(CH_2)_n$—O—$CH_2$—$CH_2$—, —$CH_2$—S—$(CH_2)_n$—, —$(CH_2)_n$—S—$CH_2$—$CH_2$—, —$CH_2$—S(O)(O)—$(CH_2)_n$—, —$(CH_2)_n$—S(O)(O)—$CH_2$—$CH_2$—, —O—C(O)—$(CH_2)_n$—, —S—C(O)—$(CH_2)_n$—, —NH—C(O)—$(CH_2)_n$—, —$CH_2$—C(O)—O—$(CH_2)_n$—, —$CH_2$—C(O)—NH—$(CH_2)_n$—, —$CH_2$—C(O)—S—$(CH_2)_n$—, —$(CH_2)_n$—C(O)—O—$CH_2$—$CH_2$—, —$(CH_2)_n$—C(O)—NH—$CH_2$—$CH_2$—, —$(CH_2)_n$—C(O)—S—$CH_2$—$CH_2$—, —$CH_2$—O—C(O)—$(CH_2)_n$—, —$CH_2$—NH—C(O)—$(CH_2)_n$—, —$CH_2$—S—C(O)—$(CH_2)_n$—, —$(CH_2)_n$—O—C(O)—$CH_2$—$CH_2$—, $(CH_2)_n$—NH—C(O)—$CH_2$—$CH_2$—, $CH_2)_n$—S—C(O)—$CH_2$—$CH_2$—, wherein n is an integer between 1 and 7;

cyclic ring-'H' is selected to be

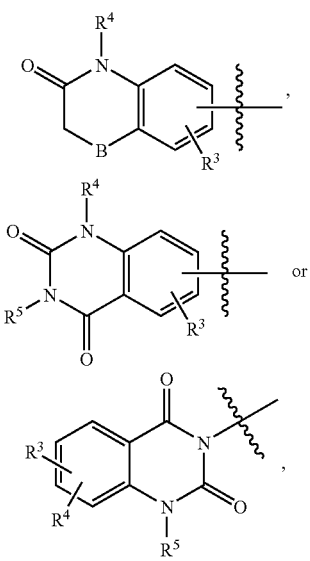

wherein 'B' is O, S, S(O)(O), or NR$^5$;

R$^2$, R$^3$, R$^4$, and R$^5$ are independently selected to be hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl, acylalkyloxycarbonyl, acyloxyalkyloxycarbonyl, acylalkyloxycarbonylamino, acyloxyalkyloxycarbonylamino, alkoxy, alkoxycarbonyl, alkoxycarbonylalkoxy, alkoxycarbonyllalkylamino, alkylasulfinyl, alkylsulfonyl, alkylthio, amino, alkylamino, arylalkylamino, dialkkylamino, arylalkoxy, arylalkoxycarbonylalkoxy, arylalkoxycarbonylalkylamino, aryloxycarbonyl, arylloxycarbonylalkoxy, aryloxycarbonylalkylamino, carboxy, carbamoyl, carbamate, carbonate, cyano, halo, heteroaryloxycarbonyl, hydroxy, phosphate, phosphonate, sulfate, sulfonate, or sulfonamide; optionally R$^2$, R$^3$, R$^4$, R$^5$, and A may substituted with isotopes that include, but not limited to $^2$H (deuterium), $^3$H (tritium), $^{13}$C, $^{15}$N, $^{18}$O, $^{17}$O, $^{31}$P, $^{32}$P, $^{35}$S, $^{18}$F and $^{36}$Cl;

R$^6$ is selected to be alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl; optionally may substituted with isotopes that include, but not limited to $^2$H (deuterium), $^3$H (tritium), $^{13}$C, $^{15}$N, $^{18}$O, $^{17}$O, $^{31}$P, $^{32}$P, $^{35}$S, $^{18}$F and $^{36}$Cl;

R$^7$ is selected to be alkyl, substituted alkyl or R$^6$ and R$^7$ together form 5- or 6-membered ring which optionally may contain one or more heteroatoms selected from O, N, or S and that may be optionally substituted with one or more substituents selected from alkyl, halo, hydroxyl, carbonyl; or together with R$^6$ forms 5- or 6-membered lactones and lactams that may be optionally substituted with one or more substituents selected from alkyl, halo, hydroxyl and carbonyl.

In another aspect of the invention, compounds comprise structural Formula (III):

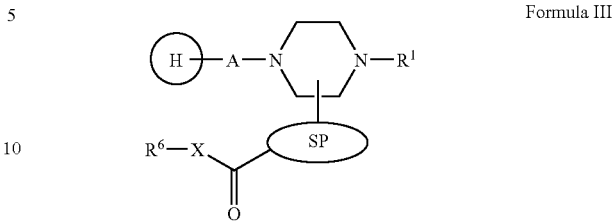

Formula III or a pharmaceutically acceptable salt, hydrate or solvate thereof, wherein X can be O, S, NH or NR$^7$;

SP is a spacer;

'A' is selected to be —O—(CH$_2$)$_n$—, —S—(CH$_2$)$_n$—, —S(O)(O)—(CH$_2$)$_n$—, —NH—(CH$_2$)$_n$—, —CH$_2$—O—(CH$_2$)$_n$—, —(CH$_2$)$_n$—O—CH$_2$—CH$_2$—, —CH$_2$—S—(CH$_2$)$_n$—, —(CH$_2$)$_n$—S—CH$_2$—CH$_2$—, —CH$_2$—S(O)(O)—(CH$_2$)$_n$—, —(CH$_2$)$_n$—S(O)(O)—CH$_2$—CH$_2$—, —O—C(O)—(CH$_2$)$_n$—, —S—C(O)—(CH$_2$)$_n$—, —NH—C(O)—(CH$_2$)$_n$—, —CH$_2$—C(O)—O—(CH$_2$)$_n$—, —CH$_2$—C(O)—NH—(CH$_2$)$_n$—, —CH$_2$—C(O)—S—(CH$_2$)$_n$—, —(CH$_2$)$_n$—C(O)—O—CH$_2$—CH$_2$—, —(CH$_2$)$_n$—C(O)—NH—CH$_2$—CH$_2$—, —(CH$_2$)$_n$—C(O)—S—CH$_2$—CH$_2$—, —CH$_2$—O—C(O)—(CH$_2$)$_n$—, —CH$_2$—NH—C(O)—(CH$_2$)$_n$—, —CH$_2$—S—C(O)—(CH$_2$)$_n$—, —(CH$_2$)$_n$—O—C(O)—CH$_2$—CH$_2$—, (CH$_2$)$_n$—NH—C(O)—CH$_2$—CH$_2$—, CH$_2$)$_n$—S—C(O)—CH$_2$—CH$_2$—, wherein n is an integer between 1 and 7;

cyclic ring-'H' is selected to be

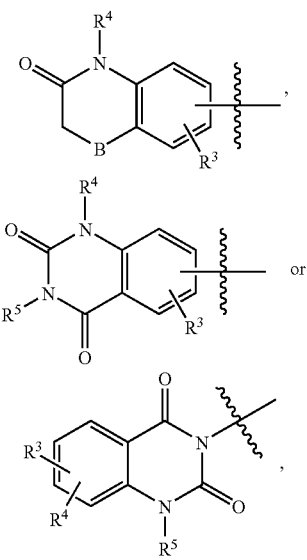

wherein 'B' is O, S, S(O)(O), or NR$^5$;

R$^1$, R$^3$, R$^4$, and R$^5$ are independently selected to be hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl, acylalkyloxycarbonyl, acyloxyalkyloxycarbonyl, acylalkyloxycarbonylamino, acyloxyalkyloxycarbonylamino, alkoxy, alkoxycarbonyl, alkoxycarbonylalkoxy, alkoxycarbonyllalkylamino, alkylasulfinyl, alkylsulfonyl, alkylthio, amino, alkylamino, arylalkylamino, dialkkylamino, arylalkoxy, arylalkoxycarbonylalkoxy, arylalkoxycarbonylalkylamino, aryloxycarbonyl, arylloxycarbonylalkoxy, aryloxycarbonylalkylamino, carboxy, carbamoyl, carbamate, carbonate, cyano, halo, heteroaryloxycarbonyl, hydroxy, phosphate, phosphonate, sulfate, sulfonate, or sulfonamide; optionally $R^1$, $R^3$, $R^4$, $R^5$ and A may substituted with isotopes that include, but not limited to $^2H$ (deuterium), $^3H$ (tritium), $^{13}C$, $^{15}N$, $^{18}O$, $^{17}O$, $^{31}P$, $^{32}P$, $^{35}S$, $^{18}F$ and $^{36}Cl$;

$R^6$ is selected to be alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl; optionally may substituted with isotopes that include, but not limited to $^2H$ (deuterium), $^3H$ (tritium), $^{13}C$, $^{15}N$, $^{18}O$, $^{17}O$, $^{31}P$, $^{32}P$, $^{35}S$, $^{18}F$ and $^{36}Cl$;

$R^7$ is selected to be alkyl, substituted alkyl or $R^6$ and $R^7$ together form 5- or 6-membered ring which optionally may contain one or more heteroatoms selected from O, N, or S and that may be optionally substituted with one or more substituents selected from alkyl, halo, hydroxyl, carbonyl; or together with $R^6$ forms 5- or 6-membered lactones and lactams that may be optionally substituted with one or more substituents selected from alkyl, halo, hydroxyl and carbonyl.

In another aspect of the invention, compounds comprise structural Formula (IV):

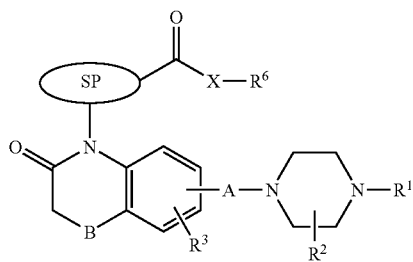

Formula IV or a pharmaceutically acceptable salt, hydrate or solvate thereof, wherein X can be O, S, NH or $NR^7$;

SP is a spacer;

'A' is selected to be —O—$(CH_2)_n$—, —S—$(CH_2)_n$—, —S(O)(O)—$(CH_2)_n$—, —NH—$(CH_2)_n$—, —$CH_2$—O—$(CH_2)_n$—, —$(CH_2)_n$—O—$CH_2$—$CH_2$—, —$CH_2$—S—$(CH_2)_n$—, —$(CH_2)_n$—S—$CH_2$—$CH_2$—, —$CH_2$—S(O)(O)—$(CH_2)_n$—, —$(CH_2)_n$—S(O)(O)—$CH_2$—$CH_2$—, —O—C(O)—$(CH_2)_n$—, —S—C(O)—$(CH_2)_n$—, —NH—C(O)—$(CH_2)_n$—, —$CH_2$—C(O)—O—$(CH_2)_n$—, —$CH_2$—C(O)—NH—$(CH_2)_n$—, —$CH_2$—C(O)—S—$(CH_2)_n$—, —$(CH_2)_n$—C(O)—O—$CH_2$—$CH_2$—, —$(CH_2)_n$—C(O)—NH—$CH_2$—$CH_2$—, —$(CH_2)_n$—C(O)—S—$CH_2$—$CH_2$—, —$CH_2$—O—C(O)—$(CH_2)_n$—, —$CH_2$—NH—C(O)—$(CH_2)_n$—, —$CH_2$—S—C(O)—$(CH_2)_n$—, —$(CH_2)_n$—O—C(O)—$CH_2$—$CH_2$—, —$(CH_2)_n$—NH—C(O)—$CH_2$—$CH_2$—, —$(CH_2)_n$—S—C(O)—$CH_2$—$CH_2$—, wherein n is an integer between 1 and 7;

'B' is O, S, S(O)(O), or $NR^5$;

$R^1$, $R^2$, $R^3$, and $R^5$ are independently selected to be hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl, acylalkyloxycarbonyl, acyloxyalkyloxycarbonyl, acylalkyloxycarbonylamino, acyloxyalkyloxycarbonylamino, alkoxy, alkoxycarbonyl, alkoxycarbonylalkoxy, alkoxycarbonyllalkylamino, alkylasulfinyl, alkylsulfonyl, alkylthio, amino, alkylamino, arylalkylamino, dialkkylamino, arylalkoxy, arylalkoxycarbonylalkoxy, arylalkoxycarbonylalkylamino, aryloxycarbonyl, arylloxycarbonylalkoxy, aryloxycarbonylalkylamino, carboxy, carbamoyl, carbamate, carbonate, cyano, halo, heteroaryloxycarbonyl, hydroxy, phosphate, phosphonate, sulfate, sulfonate, or sulfonamide; optionally $R^1$ and $R^2$ can together form a 5- or 6-membered ring which may contain one or more heteroatoms selected from O, N, or S and that ring may be optionally substituted with substituents selected from alkyl, substituted alkyl, halo, hydroxyl, and carbonyl; optionally $R^1$, $R^2$, $R^3$, $R^5$ and A may substituted with isotopes that include, but not limited to $^2H$ (deuterium), $^3H$ (tritium), $^{13}C$, $^{15}N$, $^{18}O$, $^{17}O$, $^{31}P$, $^{32}P$, $^{35}S$, $^{18}F$ and $^{36}Cl$;

$R^6$ is selected to be alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl; optionally may substituted with isotopes that include, but not limited to $^2H$ (deuterium), $^3H$ (tritium), $^{13}C$, $^{15}N$, $^{18}O$, $^{17}O$, $^{31}P$, $^{32}P$, $^{35}S$, $^{18}F$ and $^{36}Cl$;

$R^7$ is selected to be alkyl, substituted alkyl or $R^6$ and $R^7$ together form 5- or 6-membered ring which optionally may contain one or more heteroatoms selected from O, N, or S and that may be optionally substituted with one or more substituents selected from alkyl, halo, hydroxyl, carbonyl; or together with $R^6$ forms 5- or 6-membered lactones and lactams that may be optionally substituted with one or more substituents selected from alkyl, halo, hydroxyl and carbonyl.

In another aspect of the invention, compounds comprise structural Formula (V):

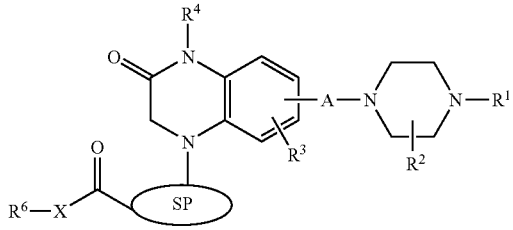

Formula V or a pharmaceutically acceptable salt, hydrate or solvate thereof, wherein X can be O, S, NH or $NR^7$;

SP is a spacer;

'A' is selected to be —O—$(CH_2)_n$—, —S—$(CH_2)_n$—, —S(O)(O)—$(CH_2)_n$—, —NH—$(CH_2)_n$—, —$CH_2$—O—$(CH_2)_n$—, —$(CH_2)_n$—O—$CH_2$—$CH_2$—, —$CH_2$—S—$(CH_2)_n$—, —$(CH_2)_n$—S—$CH_2$—$CH_2$—, —$CH_2$—S(O)(O)—$(CH_2)_n$—, —$(CH_2)_n$—S(O)(O)—$CH_2$—$CH_2$—, —O—C(O)—$(CH_2)_n$—, —S—C(O)—$(CH_2)_n$—, —NH—C(O)—$(CH_2)_n$—, —$CH_2$—C(O)—O—$(CH_2)_n$—, —$CH_2$—C(O)—NH—$(CH_2)_n$—, —$CH_2$—C(O)—S—$(CH_2)_n$—, —$(CH_2)_n$—C(O)—O—$CH_2$—

CH$_2$—, —(CH$_2$)$_n$—C(O)—NH—CH$_2$—CH$_2$—, —(CH$_2$)$_n$—C(O)—S—CH$_2$—CH$_2$—, —CH$_2$—O—C(O)—(CH$_2$)$_n$—, —CH$_2$—NH—C(O)—(CH$_2$)$_n$—, —CH$_2$—S—C(O)—(CH$_2$)$_n$—, —(CH$_2$)$_n$—O—C(O)—CH$_2$—CH$_2$—, (CH$_2$)$_n$—NH—C(O)—CH$_2$—CH$_2$—, CH$_2$)$_n$—S—C(O)—CH$_2$—CH$_2$—, wherein n is an integer between 1 and 7;

R$^1$, R$^2$, R$^3$, and R$^4$ are independently selected to be hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl, acylalkyloxycarbonyl, acyloxyalkyloxycarbonyl, acylalkyloxycarbonylamino, acyloxyalkyloxycarbonylamino, alkoxy, alkoxycarbonyl, alkoxycarbonylalkoxy, alkoxycarbonyllalkylamino, alkylasulfinyl, alkylsulfonyl, alkylthio, amino, alkylamino, arylalkylamino, dialkkylamino, arylalkoxy, arylalkoxycarbonylalkoxy, arylalkoxycarbonylalkylamino, aryloxycarbonyl, arylloxycarbonylalkoxy, aryloxycarbonylalkylamino, carboxy, carbamoyl, carbamate, carbonate, cyano, halo, heteroaryloxycarbonyl, hydroxy, phosphate, phosphonate, sulfate, sulfonate, or sulfonamide; optionally R$^1$ and R$^2$ can together form a 5- or 6-membered ring which may contain one or more heteroatoms selected from O, N, or S and that ring may be optionally substituted with substituents selected from alkyl, substituted alkyl, halo, hydroxyl, and carbonyl; optionally R$^1$, R$^2$, R$^3$, R$^4$ and A may substituted with isotopes that include, but not limited to $^2$H (deuterium), $^3$H (tritium), $^{13}$C, $^{15}$N, $^{18}$O, $^{17}$O, $^{31}$P, $^{32}$P, $^{35}$S, $^{18}$F and $^{36}$Cl;

R$^6$ is selected to be alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl; optionally may substituted with isotopes that include, but not limited to $^2$H (deuterium), $^3$H (tritium), $^{13}$C, $^{15}$N, $^{18}$O, $^{17}$O, $^{31}$P, $^{32}$P, $^{35}$S, $^{18}$F and $^{36}$Cl;

R$^7$ is selected to be alkyl, substituted alkyl or R$^6$ and R$^7$ together form 5- or 6-membered ring which optionally may contain one or more heteroatoms selected from O, N, or S and that may be optionally substituted with one or more substituents selected from alkyl, halo, hydroxyl, carbonyl; or together with R$^6$ forms 5- or 6-membered lactones and lactams that may be optionally substituted with one or more substituents selected from alkyl, halo, hydroxyl and carbonyl.

In another aspect of the invention, compounds comprise structural Formula (VI):

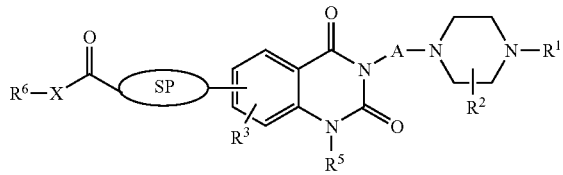

Formula VI or a pharmaceutically acceptable salt, hydrate or solvate thereof, wherein X can be O, S, NH or NR$^7$;

SP is a spacer;

'A' is selected to be —O—(CH$_2$)$_n$—, —S—(CH$_2$)$_n$—, —S(O)(O)—(CH$_2$)$_n$—, —NH—(CH$_2$)$_n$—, —CH$_2$—O—(CH$_2$)$_n$—, —(CH$_2$)$_n$—O—CH$_2$—CH$_2$—, —CH$_2$—S—(CH$_2$)$_n$—, —CH$_2$—S(O)(O)—(CH$_2$)$_n$—, —(CH$_2$)$_n$—S(O)(O)—CH$_2$—CH$_2$—, —O—C(O)—(CH$_2$)$_n$—, —S—C(O)—(CH$_2$)$_n$—, —NH—C(O)—(CH$_2$)$_n$—, —CH$_2$—C(O)—O—(CH$_2$)$_n$—, —CH$_2$—C(O)—NH—(CH$_2$)$_n$—, —CH$_2$—C(O)—S—(CH$_2$)$_n$—, —(CH$_2$)$_n$—C(O)—O—CH$_2$—CH$_2$—, —(CH$_2$)$_n$—C(O)—NH—CH$_2$—CH$_2$—, —(CH$_2$)$_n$—C(O)—S—CH$_2$—CH$_2$—, —CH$_2$—O—C(O)—(CH$_2$)$_n$—, —CH$_2$—NH—C(O)—(CH$_2$)$_n$—, —CH$_2$—S—C(O)—(CH$_2$)$_n$—, —(CH$_2$)$_n$—O—C(O)—CH$_2$—CH$_2$—, (CH$_2$)$_n$—NH—C(O)—CH$_2$—CH$_2$—, CH$_2$)$_n$—S—C(O)—CH$_2$—CH$_2$—, wherein n is an integer between 1 and 7;

R$^1$, R$^2$, R$^3$, and R$^5$ are independently selected to be hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl, acylalkyloxycarbonyl, acyloxyalkyloxycarbonyl, acylalkyloxycarbonylamino, acyloxyalkyloxycarbonylamino, alkoxy, alkoxycarbonyl, alkoxycarbonylalkoxy, alkoxycarbonyllalkylamino, alkylasulfinyl, alkylsulfonyl, alkylthio, amino, alkylamino, arylalkylamino, dialkkylamino, arylalkoxy, arylalkoxycarbonylalkoxy, arylalkoxycarbonylalkylamino, aryloxycarbonyl, arylloxycarbonylalkoxy, aryloxycarbonylalkylamino, carboxy, carbamoyl, carbamate, carbonate, cyano, halo, heteroaryloxycarbonyl, hydroxy, phosphate, phosphonate, sulfate, sulfonate, or sulfonamide; optionally R$^1$ and R$^2$ can together form a 5- or 6-membered ring which may contain one or more heteroatoms selected from O, N, or S and that ring may be optionally substituted with substituents selected from alkyl, substituted alkyl, halo, hydroxyl, and carbonyl; optionally R$^1$, R$^2$, R$^3$, R$^5$ and A may substituted with isotopes that include, but not limited to $^2$H (deuterium), $^3$H (tritium), $^{13}$C, $^{15}$N, $^{18}$O, $^{17}$O, $^{31}$P, $^{32}$P, $^{35}$S, $^{18}$F and $^{36}$Cl;

R$^6$ is selected to be alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl; optionally may substituted with isotopes that include, but not limited to $^2$H (deuterium), $^3$H (tritium), $^{13}$C, $^{15}$N, $^{18}$O, $^{17}$O, $^{31}$P, $^{32}$P, $^{35}$S, $^{18}$F and $^{36}$Cl;

R$^7$ is selected to be alkyl, substituted alkyl or R$^6$ and R$^7$ together form 5- or 6-membered ring which optionally may contain one or more heteroatoms selected from O, N, or S and that may be optionally substituted with one or more substituents selected from alkyl, halo, hydroxyl, carbonyl; or together with R$^6$ forms 5- or 6-membered lactones and lactams that may be optionally substituted with one or more substituents selected from alkyl, halo, hydroxyl and carbonyl.

In another aspect of the invention, compounds comprise structural Formula (VII):

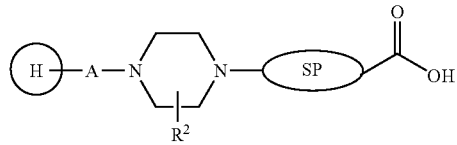

Formula VII or a pharmaceutically acceptable salt, hydrate or solvate thereof, wherein SP is a spacer;

'A' is selected to be —O—(CH$_2$)$_n$—, —S—(CH$_2$)$_n$—, —S(O)(O)—(CH$_2$)$_n$—, —NH—(CH$_2$)$_n$—, —CH$_2$—O—(CH$_2$)$_n$—, —(CH$_2$)$_n$—O—CH$_2$—CH$_2$—, —CH$_2$—S—(CH$_2$)$_n$—, —(CH$_2$)$_n$—S—CH$_2$—CH$_2$—, —CH$_2$—S(O)(O)—(CH$_2$)$_n$—, —(CH$_2$)$_n$—S(O)(O)—CH$_2$—CH$_2$—, —O—C(O)—(CH$_2$)$_n$—, —S—C(O)—(CH$_2$)$_n$—, —NH—C(O)—(CH$_2$)$_n$—, —CH$_2$—C(O)—O—(CH$_2$)$_n$—, —CH$_2$—C(O)—NH—(CH$_2$)$_n$—, —CH$_2$—C(O)—S—(CH$_2$)$_n$—, —(CH$_2$)$_n$—C(O)—O—CH$_2$—CH$_2$—, —(CH$_2$)$_n$—C(O)—NH—CH$_2$—CH$_2$—, —(CH$_2$)$_n$—C(O)—S—CH$_2$—CH$_2$—, —CH$_2$—O—C(O)—(CH$_2$)$_n$—, —CH$_2$—NH—C(O)—(CH$_2$)$_n$—, —CH$_2$—S—C(O)—(CH$_2$)$_n$—, —(CH$_2$)$_n$—O—C(O)—CH$_2$—CH$_2$—, (CH$_2$)$_n$—NH—C(O)—CH$_2$—CH$_2$—, CH$_2$)$_n$—S—C(O)—CH$_2$—CH$_2$—, wherein n is an integer between 1 and 7;

cyclic ring-'H' is selected to be

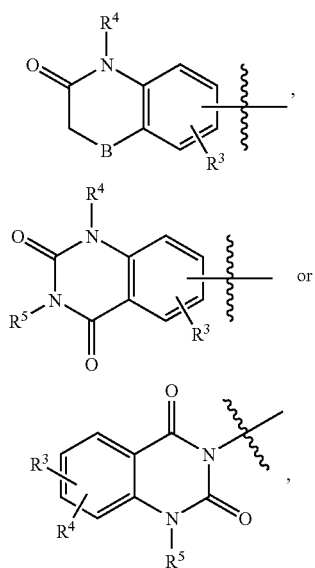

wherein 'B' is O, S, S(O)(O), or NR$^5$;

R$^2$, R$^3$, R$^4$, and R$^5$ are independently selected to be hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl, acylalkyloxycarbonyl, acyloxyalkyloxycarbonyl, acylalkyloxycarbonylamino, acyloxyalkyloxycarbonylamino, alkoxy, alkoxycarbonyl, alkoxycarbonylalkoxy, alkoxycarbonyllalkylamino, alkylasulfinyl, alkylsulfonyl, alkylthio, amino, alkylamino, arylalkylamino, dialkkylamino, arylalkoxy, arylalkoxycarbonylalkoxy, arylalkoxycarbonylalkylamino, aryloxycarbonyl, arylloxycarbonylalkoxy, aryloxycarbonylalkylamino, carboxy, carbamoyl, carbamate, carbonate, cyano, halo, heteroaryloxycarbonyl, hydroxy, phosphate, phosphonate, sulfate, sulfonate, or sulfonamide; optionally R$^2$, R$^3$, R$^4$, R$^5$, and A may substituted with isotopes that include, but not limited to $^2$H (deuterium), $^3$H (tritium), $^{13}$C, $^{15}$N, $^{18}$O, $^{17}$O, $^{31}$P, $^{32}$P, $^{35}$S, $^{18}$F and $^{36}$Cl;

In another aspect of the invention, compounds comprise structural Formula (VIII):

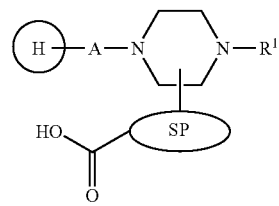

Formula VIII or a pharmaceutically acceptable salt, hydrate or solvate thereof, wherein SP is a spacer;

'A' is selected to be —O—(CH$_2$)$_n$—, —S—(CH$_2$)$_n$—, —S(O)(O)—(CH$_2$)$_n$—, —NH—(CH$_2$)$_n$—, —CH$_2$—O—(CH$_2$)$_n$—, —(CH$_2$)$_n$—O—CH$_2$—CH$_2$—, —CH$_2$—S—(CH$_2$)$_n$—, —(CH$_2$)$_n$—S—CH$_2$—CH$_2$—, —CH$_2$—S(O)(O)—(CH$_2$)$_n$—, —(CH$_2$)$_n$—S(O)(O)—CH$_2$—CH$_2$—, —O—C(O)—(CH$_2$)$_n$—, —S—C(O)—(CH$_2$)$_n$—, —NH—C(O)—(CH$_2$)$_n$—, —CH$_2$—C(O)—O—(CH$_2$)$_n$—, —CH$_2$—C(O)—NH—(CH$_2$)$_n$—, —CH$_2$—C(O)—S—(CH$_2$)$_n$—, —(CH$_2$)$_n$—C(O)—O—CH$_2$—CH$_2$—, —(CH$_2$)$_n$—C(O)—NH—CH$_2$—CH$_2$—, —(CH$_2$)$_n$—C(O)—S—CH$_2$—CH$_2$—, —CH$_2$—O—C(O)—(CH$_2$)$_n$—, —CH$_2$—NH—C(O)—(CH$_2$)$_n$—, —CH$_2$—S—C(O)—(CH$_2$)$_n$—, —(CH$_2$)$_n$—O—C(O)—CH$_2$—CH$_2$—, (CH$_2$)$_n$—NH—C(O)—CH$_2$—CH$_2$—, CH$_2$)$_n$—S—C(O)—CH$_2$—CH$_2$—, wherein n is an integer between 1 and 7;

cyclic ring-'H' is selected to be

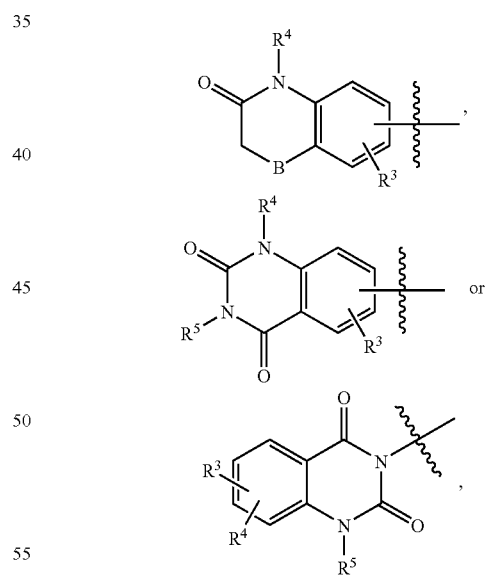

wherein 'B' is O, S, S(O)(O), or NR$^5$;

R$^1$, R$^3$, R$^4$, and R$^5$ are independently selected to be hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl, acylalkyloxycarbonyl, acyloxyalkyloxycarbonyl, acylalkyloxycarbonylamino, acyloxyalkyloxycarbonylamino, alkoxy, alkoxycarbonyl, alkoxycarbonylalkoxy, alkoxycarbonyllalkylamino, alkylasulfinyl, alkylsulfonyl, alkylthio, amino, alkylamino, arylalkylamino, dialkkylamino, arylalkoxy, arylalkoxycarbonylalkoxy, arylalkoxycarbonylalkylamino, aryloxycarbonyl, arylloxycarbonylalkoxy, aryloxycarbonylalkylamino, carboxy, carbamoyl, carbamate, carbonate, cyano, halo, heteroaryloxycarbonyl, hydroxy, phosphate, phosphonate, sulfate, sulfonate, or sulfonamide; optionally $R^1$, $R^3$, $R^4$, $R^5$ and A may substituted with isotopes that include, but not limited to $^2H$ (deuterium), $^3H$ (tritium), $^{13}C$, $^{15}N$, $^{18}O$, $^{17}O$, $^{31}P$, $^{32}P$, $^{35}S$, $^{18}F$ and $^{36}Cl$;

In another aspect of the invention, compounds comprise structural Formula (IX):

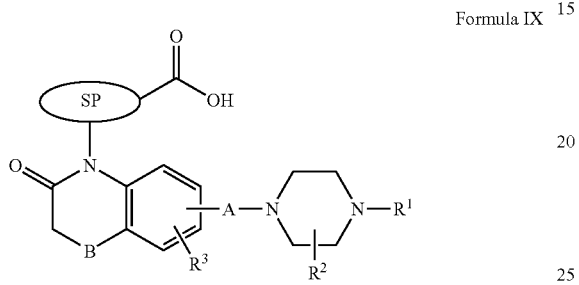

Formula IX or a pharmaceutically acceptable salt, hydrate or solvate thereof, wherein SP is a spacer;

'A' is selected to be —O—$(CH_2)_n$—, —S—$(CH_2)_n$—, —S(O)(O)—$(CH_2)_n$—, —NH—$(CH_2)_n$—, —$CH_2$—O—$(CH_2)_n$—, —$(CH_2)_n$—O—$CH_2$—$CH_2$—, —$CH_2$—S—$(CH_2)_n$—, —$(CH_2)_n$—S—$CH_2$—$CH_2$—, —$CH_2$—S(O)(O)—$(CH_2)_n$—, —$(CH_2)_n$—S(O)(O)—$CH_2$—$CH_2$—, —O—C(O)—$(CH_2)_n$—, —S—C((O)—$(CH_2)_n$—, —NH—C(O)—$(CH_2)_n$—, —$CH_2$—C(O)—O—$(CH_2)_n$—, —$CH_2$—C(O)—NH—$(CH_2)_n$—, —$CH_2$—C(O)—S—$(CH_2)_n$—, —$(CH_2)_n$—C(O)—O—$CH_2$—$CH_2$—, —$(CH_2)_n$—C(O)—NH—$CH_2$—$CH_2$—, —$(CH_2)_n$—C(O)—S—$CH_2$—$CH_2$—, —$CH_2$—O—C(O)—$(CH_2)_n$—, —$CH_2$—NH—C(O)—$(CH_2)_n$—, —$CH_2$—S—C(O)—$(CH_2)_n$—, —$(CH_2)_n$—O—C(O)—$CH_2$—$CH_2$—, $(CH_2)_n$—NH—C(O)—$CH_2$—$CH_2$—, $CH_2)_n$—S—C(O)—$CH_2$—$CH_2$—, wherein n is an integer between 1 and 7;

'B' is O, S, S(O)(O), or $NR^5$;

$R^1$, $R^2$, $R^3$, and $R^5$ are independently selected to be hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl, acylalkyloxycarbonyl, acyloxyalkyloxycarbonyl, acylalkyloxycarbonylamino, acyloxyalkyloxycarbonylamino, alkoxy, alkoxycarbonyl, alkoxycarbonylalkoxy, alkoxycarbonyllalkylamino, alkylasulfinyl, alkylsulfonyl, alkylthio, amino, alkylamino, arylalkylamino, dialkkylamino, arylalkoxy, arylalkoxycarbonylalkoxy, arylalkoxycarbonylalkylamino, aryloxycarbonyl, arylloxycarbonylalkoxy, aryloxycarbonylalkylamino, carboxy, carbamoyl, carbamate, carbonate, cyano, halo, heteroaryloxycarbonyl, hydroxy, phosphate, phosphonate, sulfate, sulfonate, or sulfonamide; optionally $R^1$ and $R^2$ can together form a 5- or 6-membered ring which may contain one or more heteroatoms selected from O, N, or S and that ring may be optionally substituted with substituents selected from alkyl, substituted alkyl, halo, hydroxyl, and carbonyl; optionally $R^1$, $R^2$, $R^5$ and A may substituted with isotopes that include, but not limited to $^2H$ (deuterium), $^3H$ (tritium), $^{13}C$, $^{15}N$, $^{18}O$, $^{17}O$, $^{31}P$, $^{32}P$, $^{35}S$, $^{18}F$ and $^{36}Cl$;

In another aspect of the invention, compounds comprise structural Formula (X):

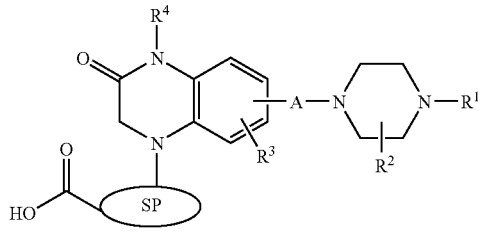

Formula X or a pharmaceutically acceptable salt, hydrate or solvate thereof, wherein SP is a spacer;

'A' is selected to be —O—$(CH_2)_n$—, —S—$(CH_2)_n$—, —S(O)(O)—$(CH_2)_n$—, —NH—$(CH_2)_n$—, —$CH_2$—O—$(CH_2)_n$—, —$(CH_2)_n$—O—$CH_2$—$CH_2$—, —$CH_2$—S—$(CH_2)_n$—, —$(CH_2)_n$—S—$CH_2$—$CH_2$—, —$CH_2$—S(O)(O)—$(CH_2)_n$—, —$(CH_2)_n$—S(O)(O)—$CH_2$—$CH_2$—, —O—C(O)—$(CH_2)_n$—, —S—C(O)—$(CH_2)_n$—, —NH—C(O)—$(CH_2)_n$—, —$CH_2$—C(O)—O—$(CH_2)_n$—, —$CH_2$—C(O)—NH—$(CH_2)_n$—, —$CH_2$—C(O)—S—$(CH_2)_n$—, —$(CH_2)_n$—C(O)—O—$CH_2$—$CH_2$—, —$(CH_2)_n$—C(O)—NH—$CH_2$—$CH_2$—, —$(CH_2)_n$—C(O)—S—$CH_2$—$CH_2$—, —$CH_2$—O—C(O)—$(CH_2)_n$—, —$CH_2$—NH—C(O)—$(CH_2)_n$—, —$CH_2$—S—C(O)—$(CH_2)_n$—, —$(CH_2)_n$—O—C(O)—$CH_2$—$CH_2$—, $(CH_2)_n$—NH—C(O)—$CH_2$—$CH_2$—, $CH_2)_n$—S—C(O)—$CH_2$—$CH_2$—, wherein n is an integer between 1 and 7;

$R^1$, $R^2$, $R^3$, and $R^4$ are independently selected to be hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl, acylalkyloxycarbonyl, acyloxyalkyloxycarbonyl, acylalkyloxycarbonylamino, acyloxyalkyloxycarbonylamino, alkoxy, alkoxycarbonyl, alkoxycarbonylalkoxy, alkoxycarbonyllalkylamino, alkylasulfinyl, alkylsulfonyl, alkylthio, amino, alkylamino, arylalkylamino, dialkkylamino, arylalkoxy, arylalkoxycarbonylalkoxy, arylalkoxycarbonylalkylamino, aryloxycarbonyl, arylloxycarbonylalkoxy, aryloxycarbonylalkylamino, carboxy, carbamoyl, carbamate, carbonate, cyano, halo, heteroaryloxycarbonyl, hydroxy, phosphate, phosphonate, sulfate, sulfonate, or sulfonamide; optionally $R^1$ and $R^2$ can together form a 5- or 6-membered ring which may contain one or more heteroatoms selected from O, N, or S and that ring may be optionally substituted with substituents selected from alkyl, substituted alkyl, halo, hydroxyl, and carbonyl; optionally $R^1$, $R^2$, $R^3$, $R^4$ and A may substituted with isotopes that include, but not limited to $^2H$ (deuterium), $^3H$ (tritium), $^{13}C$, $^{15}N$, $^{18}O$, $^{17}O$, $^{31}P$, $^{32}P$, $^{35}S$, $^{18}F$ and $^{36}Cl$;

In another aspect of the invention, compounds comprise structural Formula (XI):

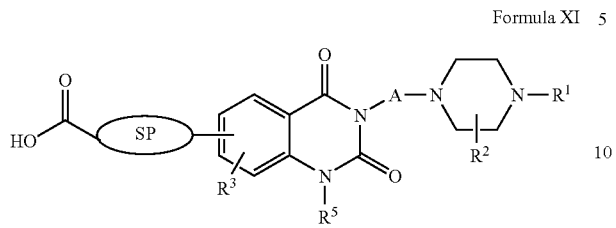

Formula XI or a pharmaceutically acceptable salt, hydrate or solvate thereof, wherein SP is a spacer;

'A' is selected to be —O—(CH$_2$)$_n$—, —S—(CH$_2$)$_n$—, —S(O)(O)—(CH$_2$)$_n$—, —NH—(CH$_2$)$_n$—, —CH$_2$—O—(CH$_2$)$_n$—, —(CH$_2$)$_n$—O—CH$_2$—CH$_2$—, —CH$_2$—S—(CH$_2$)$_n$—, —(CH$_2$)$_n$—S—CH$_2$—CH$_2$—, —CH$_2$—S(O)(O)—(CH$_2$)$_n$—, —(CH$_2$)$_n$—S(O)(O)—CH$_2$—CH$_2$—, —O—C(O)—(CH$_2$)$_n$—, —S—C(O)—(CH$_2$)$_n$—, —NH—C(O)—(CH$_2$)$_n$—, —CH$_2$—C(O)—O—(CH$_2$)$_n$—, —CH$_2$—C(O)—NH—(CH$_2$)$_n$—, —CH$_2$—C(O)—S—(CH$_2$)$_n$—, —(CH$_2$)$_n$—C(O)—O—CH$_2$—CH$_2$—, —(CH$_2$)$_n$—C(O)—NH—CH$_2$—CH$_2$—, —(CH$_2$)$_n$—C(O)—S—CH$_2$—CH$_2$—, —CH$_2$—O—C(O)—(CH$_2$)$_n$—, —CH$_2$—NH—C(O)—(CH$_2$)$_n$—, —CH$_2$—S—C(O)—(CH$_2$)$_n$—, —(CH$_2$)$_n$—O—C(O)—CH$_2$—CH$_2$—, —(CH$_2$)$_n$—NH—C(O)—CH$_2$—CH$_2$—, —(CH$_2$)$_n$—S—C(O)—CH$_2$—CH$_2$—, wherein n is an integer between 1 and 7;

R$^1$, R$^2$, R$^3$, and R$^5$ are independently selected to be hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl, acylalkyloxycarbonyl, acyloxyalkyloxycarbonyl, acylalkyloxycarbonylamino, acyloxyalkyloxycarbonylamino, alkoxy, alkoxycarbonyl, alkoxycarbonylalkoxy, alkoxycarbonyllalkylamino, alkylasulfinyl, alkylsulfonyl, alkylthio, amino, alkylamino, arylalkylamino, dialkkylamino, arylalkoxy, arylalkoxycarbonylalkoxy, arylalkoxycarbonylalkylamino, aryloxycarbonyl, arylloxycarbonylalkoxy, aryloxycarbonylalkylamino, carboxy, carbamoyl, carbamate, carbonate, cyano, halo, heteroaryloxycarbonyl, hydroxy, phosphate, phosphonate, sulfate, sulfonate, or sulfonamide; optionally R$^1$ and R$^2$ can together form a 5- or 6-membered ring which may contain one or more heteroatoms selected from O, N, or S and that ring may be optionally substituted with substituents selected from alkyl, substituted alkyl, halo, hydroxyl, and carbonyl; optionally R$^1$, R$^2$, R$^3$ R$^5$ and A may substituted with isotopes that include, but not limited to $^2$H (deuterium), $^3$H (tritium), $^{13}$C, $^{15}$N, $^{18}$O, $^{17}$O, $^{31}$P, $^{32}$P, $^{35}$S, $^{18}$F and $^{36}$Cl;

The compounds of this invention described herein can have one or more of the following characteristics or properties:

(a) Compounds of the invention can have affinity for dopamine D$_2$ receptors;
(b) Compounds of the invention can have affinity for serotonin 5-HT$_{1A}$ receptors;
(c) Compounds of the invention can have affinity for serotonin 5-HT$_{2A}$ receptors;
(d) Compounds according to the invention contain at least one hydrolysable bond that can be cleaved non-oxidatively by hydrolytic enzyme(s);
(e) The primary metabolites of compounds result from a non-oxidative metabolic pathway;
(f) The primary metabolite(s), regardless of the electrophysiological properties of the parent drug, has, or have, negligible inhibitory activity at the HERG (human ether-a-go-go related gene) potassium channel at the normal therapeutic concentration of the parent drug in plasma (e.g. the concentration of the metabolite must be at least five times higher than the normal therapeutic concentration of the parent compound before activity at the HERG potassium channel is observed);
(g) Compounds of the invention, as well as the metabolites thereof, do not cause, or have reduced incidence of metabolic drug-drug interaction (DDI) when co-administered with other drugs;
(h) Compounds of the invention, as well as metabolites thereof, do not substantially elevate liver function test (LFT) values when administered alone;
(i) Oral bioavailability of the compounds is consistent with oral administration using standard pharmacological oral formulations; however, the compounds, and compositions thereof, can also be administered using any delivery system that produces constant and controllable blood levels overt time.

In one aspect, the invention provides compounds having any two or more of the above identified characteristics or properties. In another aspect, the invention provides for compounds having at least any three or more of the above identified properties or characteristics. In yet another aspect, the compounds, and compositions thereof, have any combination of four to seven of the above identified characteristics or properties. Preferably, the compounds of the invention have all nine characteristics or properties.

Preferably, the primary metabolite(s) of the inventive compounds, regardless of the electrophysiological properties of the parent drug, has, or have, negligible inhibitory activity at the HERG potassium channel at normal therapeutic concentrations of the drug in plasma. In other words, the concentration of the metabolite can be at least five times higher than the normal therapeutic concentration of the parent compound before activity at the HERG potassium channel is observed. Preferably, the concentration of the metabolite can be at least ten times higher than the normal therapeutic concentration of the parent compound before activity at the HERG potassium channel is observed.

Compounds according to the invention are primarily metabolized by endogenous hydrolytic enzymes via hydrolysable bonds engineered into their structures. The primary metabolites resulting from this metabolic pathway are water soluble and do not have, or show a reduced incidence of, DDI when administered with other medications (drugs). Non-limiting examples of hydrolysable bonds that can be incorporated into compounds according to the invention include amide, ester, carbamate, carbonate, phosphate, sulfate, urea, glycoside, or other bonds that can be cleaved by hydrolases.

Additional modifications of the compounds disclosed herein can readily be made by those skilled in the art. Thus, analogs and salts of the exemplified compounds are within the scope of the subject invention. With knowledge of the compounds of the subject invention skilled artisans can use known procedures to synthesize these compounds from available substrates. As used in this application, the term "analogs" refers to compounds which are substantially the same as another compound but which may have been modified by, for example, adding additional side groups. The term "analogs" as used in this application also may refer to compounds which are substantially the same as another compound but which have atomic or molecular substitution at certain locations in the compound.

The subject invention further pertains to enantiomerically isolated compounds, and compositions comprising the compounds. The isolated enantiomeric forms of the compounds of the invention are substantially free from one another (i.e., in enantiomeric excess). In other words, the "R" forms of the compounds are substantially free from the "S" forms of the compounds and are, thus, in enantiomeric excess of the "S" forms. Conversely, "S" forms of the compounds are substantially free of "R" forms of the compounds and are, thus, in enantiomeric excess of the "R" forms. In one embodiment of the invention, the isolated enantiomeric compounds are at least about in 80% enantiomeric excess. Thus, for example, the compounds are at least about 90% enantiomeric excess, preferably at least about 95% enantiomeric excess, more preferably at least about 97% enantiomeric excess., or even more preferably, at least 99% or greater than 99% enantiomeric excess.

Synthesis of the Compounds of the Invention

The compounds of the invention can be obtained via the synthetic methods illustrated in Schemes 1-5. Those of skill in the art will appreciate that a preferred synthetic route to the compounds of the invention will consist of attaching or incorporating soft-moieties to piperazine derivatives of Formulae (I)-(XI). Several methods have been described in the art for the synthesis of piperazine derivatives. Other methods are known in the art for synthesizing piperazine derivatives, which are readily accessible to the skilled artisan. The soft-moieties attached to spacers thereof are commercially available or can be prepared by established procedures (See e.g., Green et al., "Protective Groups in Organic Chemistry," (Wiley, 4th ed., 2006); Harrison et al "Compendium of Synthetic Organic Methods," vols. 1-8 (John Wiley and Sons, 1971-1996); "Beilstein Handbook of Organic Chemistry, Frankfurt, Germany; Feiser et al, "Reagents for Organic Synthesis," Volumes 1-45, Karger, 1991; March, Advanced Organic Chemistry," Wiley Interscience, 4$^{th}$ ed., 1991; Larock "Comprehensive Organic Transformations," Wiley-VCH Publishers, 2$^{nd}$ ed., 1999; Paquette, "Encyclopedia of Reagents for Organic Synthesis," John Wiley and Sons, 1$^{st}$ ed., 1995).

Accordingly, starting materials useful for preparing compounds of the invention and intermediates thereof are commercially available or can be prepared by well-known synthetic methods. Other methods for the synthesis of piperazine derivatives described herein are either described in the art or will be readily apparent to the skilled artisan in view of the references provided above and may be used to synthesize the compounds of the invention. Accordingly, the methods presented in the Schemes herein are illustrative rather than comprehensive.

In one method piperazine derivatives comprising Formulae (I)-(VI) were can be prepared as described in Scheme 1. The commercially available starting building block 6-nitro-2H-1,4-benzoxazin-3(4H)-one 1 was purchased from Sigma-Aldrich. The nitrobenzoxazinone 1 was treated with potassium borohydride (KBH$_4$) in presence of copper (I) chloride (CuCl) in methanol at 25° C. to get 6-aminobonzoxazinone 2 in good yield. The intermediate benzoxazinone 2 was coupled with substituted piperazinylbutanoic acids 3 under standard coupling conditions using activating agent dicyclohexylcarbodiimide (DCC) in presence of a milde base N,N-dimethylaminopyridine (DMAP) in 1:1 mixture of dichloromethane (DCM) and tetrahydrofuran (THF) as solvent at room temperature to give the the benzoxazinylamides 4. The target piperazine hydrochloride salts 5 were prepared by treating the amides 4 with 2M ethereal solution of hydrogen chloride (Hal) in DCM at room temperature in excellent yields.

Scheme 1

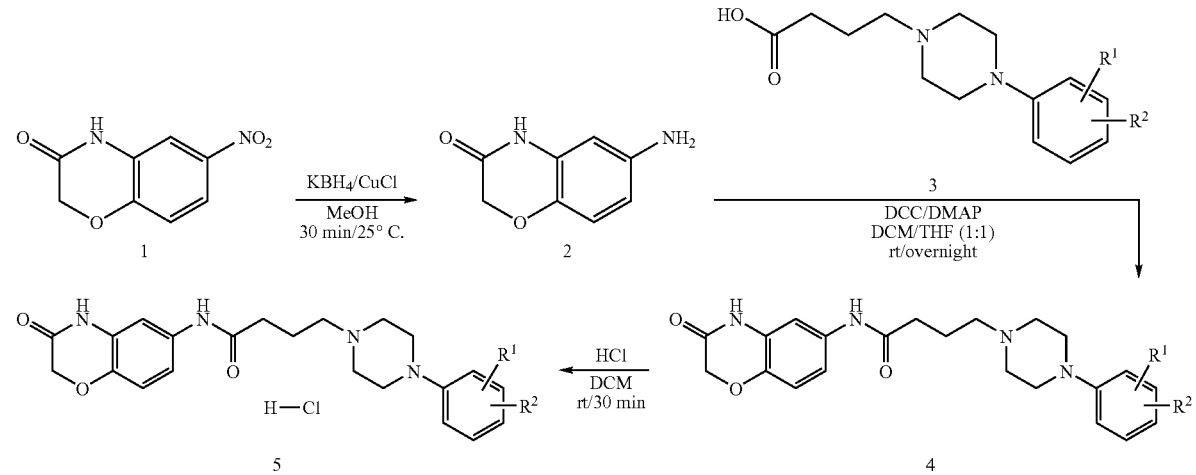

a) R$^1$ = 2-OMe, R$^2$ = H;
b) R$^1$ = 2-Cl, R$^2$ = 3-Cl

The synthetic intermediates piperazinylbutanoic acids 3 were prepared as described in Scheme 2. The substituted piperazines 7 were purchased from Sigma-Aldrich and alkylated with ethyl 4-bromobutanoate 6a under standard alkylating conditions using diisopropylethylamine (DIEA) as base in anhydrous acetonitrile to give pipazine esters 8. The piperazinylbutanoic acids 3 were prepared by saponification of the corresponding esters 8 in good yields.

Scheme 2

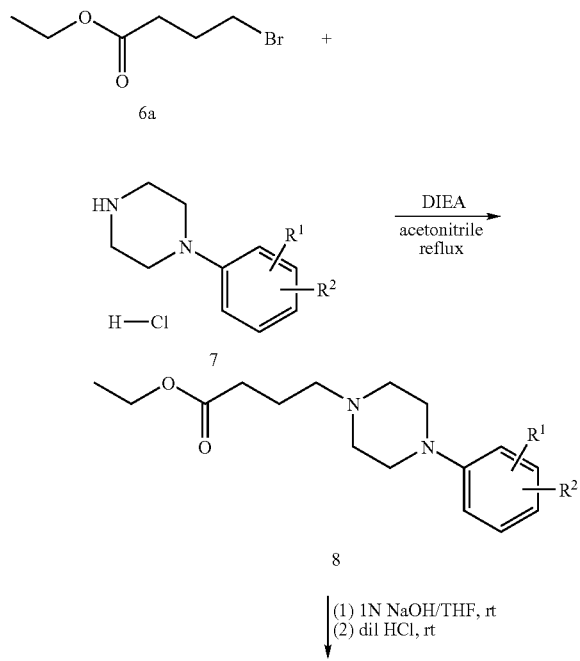

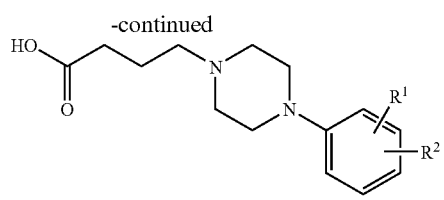

3a, R¹ = 2-OMe, R² = H
3b, R¹ = 2-Cl, R² = 3-Cl

In another method selected piperazine derivatives comprising Formulae (I)-(VI) were prepared as described in Scheme 3. The starting building block 4-methoxy-2-nitrophenol 9 was purchased from Sigma-Aldrich. The phenol 9 was alkylated with ethyl bromoacetate 6d under standard alkylation conditions using mild base, potassium carbonate (K₂CO₃) in acetone to give the methoxynitrophenylester 11 in good yield. The ester 11 was treated with aluminum chloride (AlCl₃) in DCM at relux temperature to give the nitrophenol 12. The nitrophenyloxyalkylbromide 14 was prepared by alkylating the nitrophenol 12 with 1,4-dibromobutane 13 under similar reaction conditions described for the synthesis of nitrophenylester 11 in good yield. The nitrophenyloxyalkylbromide 14 was coupled with substituted piperazines 15 under standard alkylating conditions using DIEA as base and anhydrous acetonitrile as solvent to give the piperazine derivaties 16. The treatment of piperazine derivatives with iron in presence of iron (ITT) chloride hexahydrate (FeCl₃.6H₂O) in a mixture of solvents ethanol and acetic acid at reflux temperature gave the corresponding piperazine derivatives 17. The target piperazine hydrochloride salts 18 were prepared by treating the piperazines 17 with 2M ethereal solution of hydrogen chloride (Hal) in DCM at room temperature in excellent yields Scheme 3

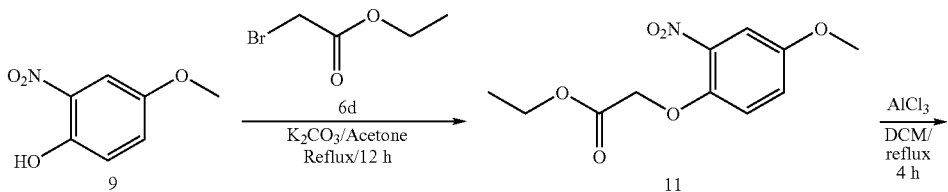

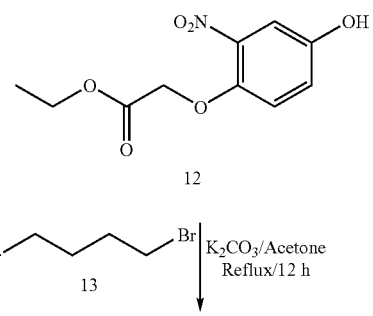

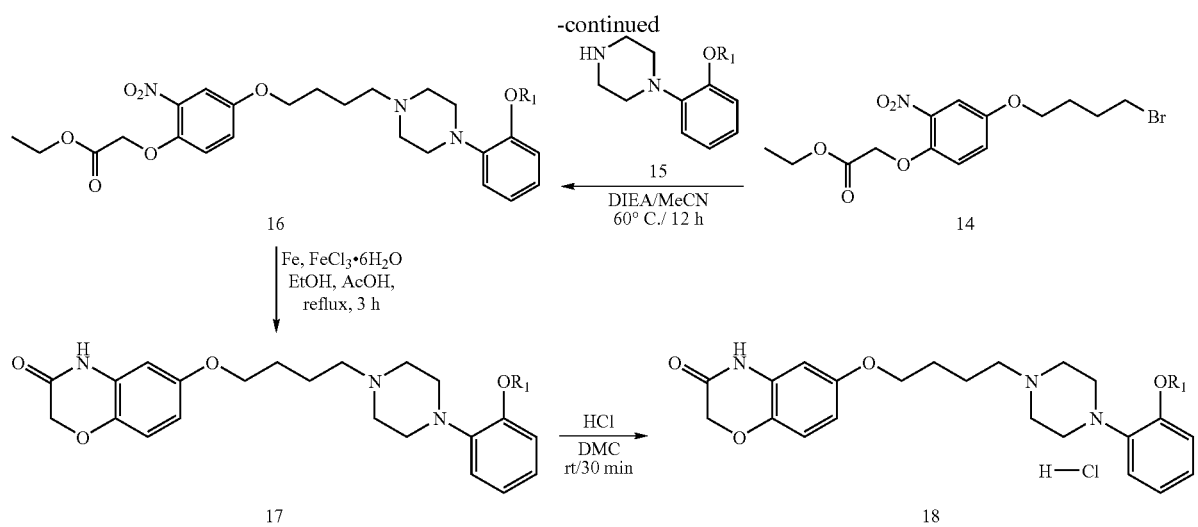

The synthetic intermediates 15 were prepared in overall good yields as described in Scheme 4. The commercially available 2-hydroxyphenylpiperazine 19 was purchased from Sigma-Aldrich. The piperazine 19 was reacted with di-tert-butylcarbonate (BOC$_2$O) in THF at reflux temperature to get the BOC-protected piperazine derivative 20. The piperazine 20 was alkylated with bromoalkylcarboxylic acid esters 6 using cesium carbonate (Cs$_2$CO$_3$) in N,N-dimethylformamide (DMF) at around 70° C. to give the BOC-protected piperazine derivatives 21. The deprotection of the BOC group by treating with trifluoroacetic acid (TFA) in DCM at room temperature gave the piperazine intermediates 15 as TFA salt in good yields. The TFA salt form of the piperazines 15 were used without any purification in the synthesis of piperazine derivatives 16.

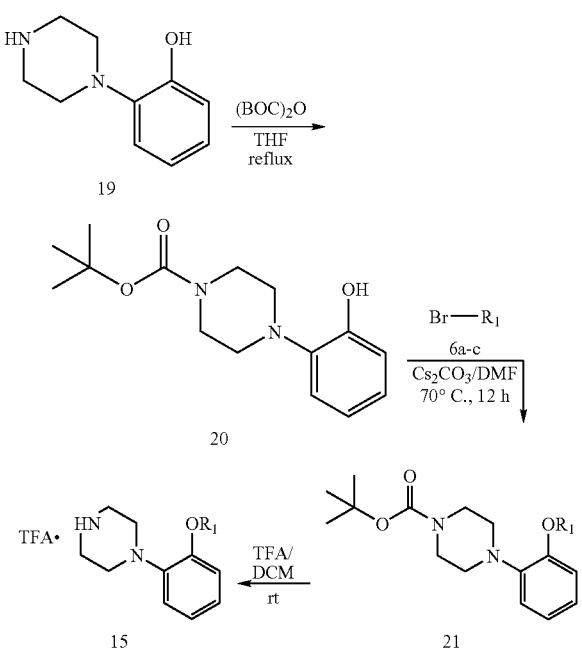

In another method selected piperazine derivatives comprising Formulae (I)-(VI) were prepared as described in the Scheme 5. The starting building block 6-acetyl-2H-1,4-benzoxazin-3-(4H)-one 22 was purchased from Sigma-Aldrich. The benzoxazinone 22 was alkylated with appropriate bromoalkylcarboxylic acid ester 6 in presence of a mild base K$_2$CO$_3$ in acetone at reflux temperature to give the alkylated benzoxazinone 23 in good yield. The benzoxazinone s 23 were subjected to Baeyer-Villiger oxidation conditions using trifluoroacetic anhydride (TFAA) and urea hydrogen peroxide (UHP) in presence of sodium hydrogen carbonate (NaHCO$_3$) in DCM as solvent at 0° C. to room temperature to give the corresponding acetoxy derivative 24. The treatment of compounds 24 with morpholine in THF at reflux temperature gave the hydroxybenzoxazine derivates 25 in good yields. The hydroxybenoxazine derivatives were alkylated with 1,4-dibromobutane 13 following the reaction conditions described for the synthesis of compound 14 as illustrated in Scheme 3 to give the benzoxazine derivatives 26. The intermediates 26 were further coupled with appropriate substituted piperazines 7 using DIEA as base in acetonitrile as solvent to give the target piperazine derivatives 27 in good yields. The hydrochloride salts 28 of the target piperazines 27 were prepared by treating them with 2M ethereal solution of hydrogen chloride (Hal) in DCM at room temperature in quantitative yields.

Scheme 5
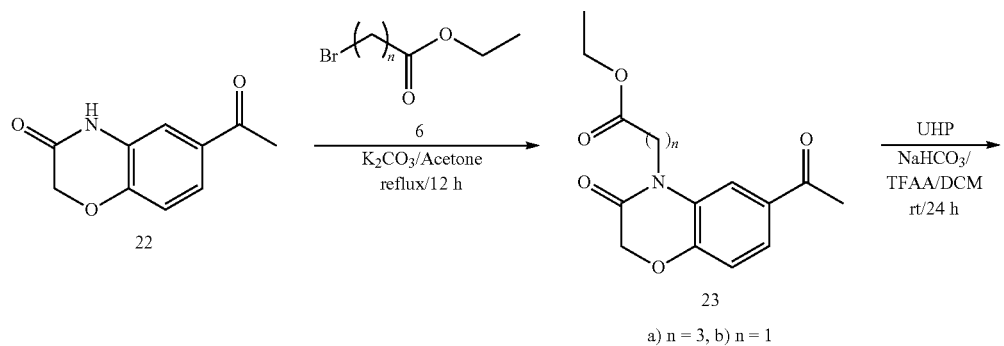
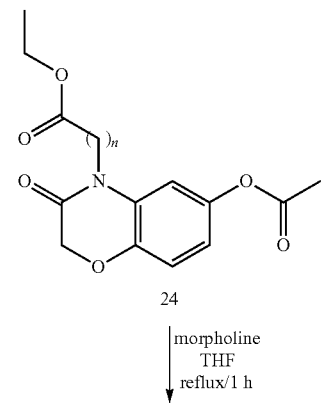
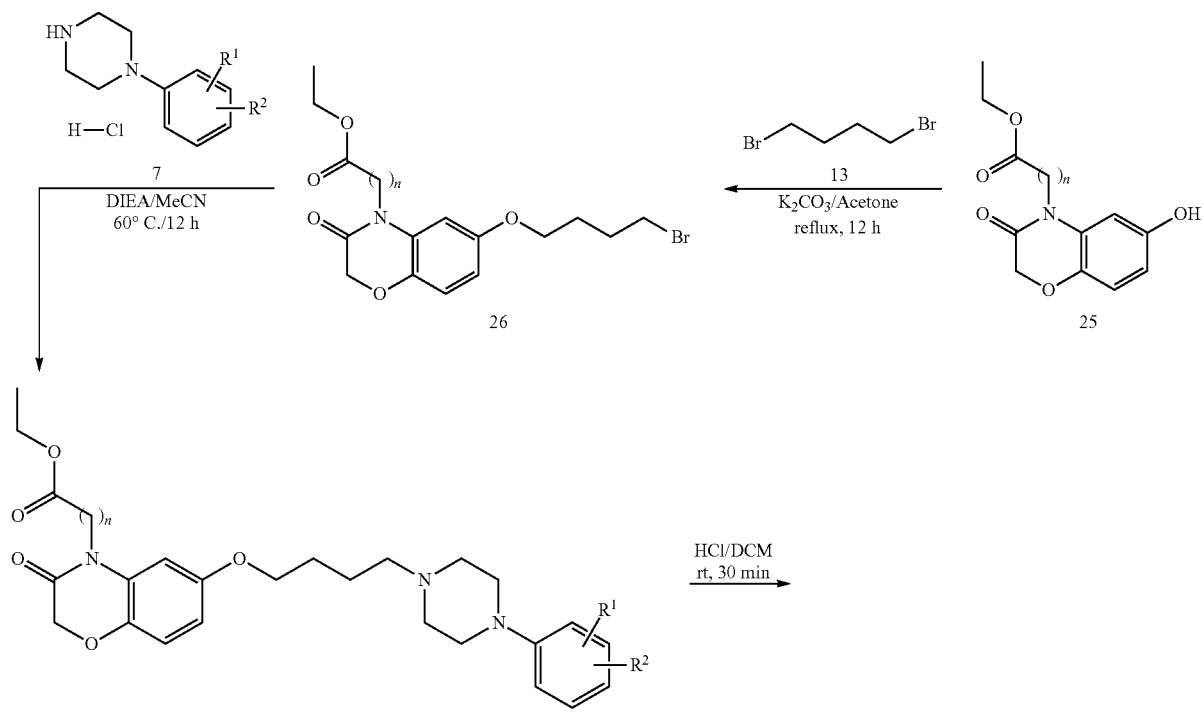

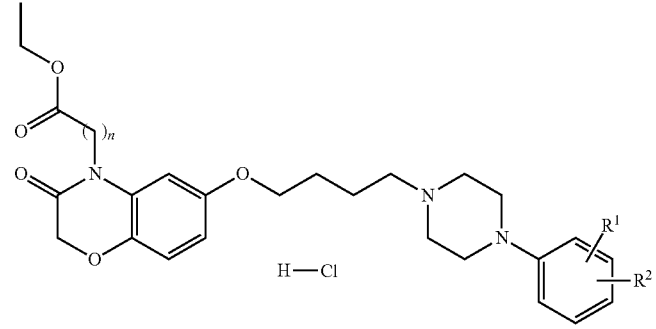

27-28a, R$^1$ = 2-OMe, R$^2$ = H; n = 3
27-28b, R$^1$ = 2-Cl, R$^2$ = 3-Cl; n = 3
27-28c, R$^1$ = 2-Cl, R$^2$ = 3-Cl; n = 1

In another method the selected piperazine derivatives comprising the Formulae (VII)-(XI) can be prepared from the appropriate piperazine derivatives comprising the Formulae (I)-(VI) by hydrolyzing the soft moieties on them using well known reaction conditions in the field. For example, a piperazine derivative carrying an ester group as soft moiety as in the Formulae (I)-(VI) can be hydrolysed using standard saponification method to give the corresponding piperazine derivative carrying a carboxylic acid group as in the Formulae (VII)-(XI). Similarly, the appropriate piperazines comprising the Formulae (I)-(VI) carrying other soft moiety like amide can also be cleaved under standard reaction conditions to give the piperazine derivatives comprising the Formulae (VII)-(XI).

Therapeutic Uses of Compounds of Structural Formulae (I)-(XI)

The present invention relates to synthesis, compositions and methods of using piperazine based compounds which are useful for treating schizophrenia and related psychoses such as acute maniac, bipolar disorder, autistic disorder and depression. The present invention provides methods for synthesizing such quinolinone based antipsychotic agents. The present invention also provides methods for using piperazine based antipsychotic agents and composition of quinolinone based antipsychotic agents for treating schizophrenia and related psychoses such as acute maniac, bipolar disorder, autistic disorder and depression.

In accordance with the invention, a compound and/or a composition containing a compound of structural Formulae (I)-(XI) is administered to a patient, preferably a human, suffering from schizoprenia. Further, in certain embodiments, the compounds and/or compositions of the invention are administered to a patient, preferably a human, as a treatment or preventive measure against acute manic, bipolar disorder, autistic disorder and depression.

Thus, those of skill in the art may readily assay and use the compounds and/or compositions containing compound(s) of structural Formulae (I)-(XI) to treat a medical condition for which an antipsychotic is desired.

Therapeutic/Prophylactic Administration

The compounds, and/or compositions containing compounds(s), of structural Formulae (I)-(XI) can be advantageously used in human medicine. As previously described in detail above, compounds and compositions containing compound(s) of structural Formulae (I)-(XI) are useful for the treatment of schizophrenia and related psychoses such as acute manic, bipolar disorder, autistic disorder and depression.

When used to treat or prevent the above disease or disorders compounds and/or compositions of the invention can be administered or applied singly, in combination with other agents. The compounds and/or compositions of the invention can also be administered or applied singly, in combination with other pharmaceutically active agents, including other compounds and/or compositions of the invention.

The current invention provides methods of treatment and prophylaxis by administration to a patient of a therapeutically effective amount of a composition and/or compound of the invention. The patient may be an animal, is more preferably a mammal, and most preferably a human.

The present compounds and/or compositions of the invention, which comprise one or more compounds and/or compositions of the invention are preferably administered orally. The compounds and/or compositions of the invention may also be administered by any other convenient route, for example, by infusion or bolus injection, by absorption through epithelial or mucocutaneous linings (e.g., oral mucosa, rectal and intestinal mucosa, etc.). Administration can be systemic or local. Various delivery systems are known, (e.g., encapsulation in liposomes, microparticles, microcapsules, capsules, etc.) that can be used to administer a compound and/or composition of the invention. Methods of administration include, but are not limited to, intradermal, intramuscular, intraperitoneal, intravenous, subcutaneous, intranasal, epidural, oral, sublingual, intranasal, intracerebral, intravabinal, transdermal, rectally, by inhalation, or topically, particularly to the ears, nose, eyes or skin.

In particularly, preferred embodiments, the compounds and/or compositions of the invention can be delivered via sustained release systems, preferably oral sustained release systems. In one embodiment, a pump may be used (see, Langer, supra; Sefton, 1987, CRC Crit. Ref Biomed. Eng. 14:201; Saudek et al., 1989, N. Engl. J. Med. 321:574).

In another embodiment, polymeric materials can be used (see "Medical Applications of Controlled Release," Langer and Wise (eds.), Wiley, New York (1984); Ranger and Peppas, 1983, J. Macromol. Sci. Rev. Macromol Chem. 23:61; see also Levy et al., 1985, Science 228:190; During et al., 1989, Ann. Neurol. 25:351; Howard et al, 1989, J. Neurosurg. 71:105). In a preferred embodiment, polymeric materials are used for oral sustained release delivery. Preferred polymers include sodium carboxymethylcellulose, hydroxypropylcellulose, hydroxypropylmethylcellulose and hydroxyethylcellulose (most preferred, hydroxypropylmethylcellulose). Other preferred cellulose ethers have been described in the art (Bamba et al., Int. J. Pharm., 1979, 2, 307).

In another embodiment, enteric-coated preparations can be used for oral sustained release administration. Preferred coating materials include polymers with a pH-dependent solubility (i.e., pH-controlled release), polymers with a slow or pH-dependent rate of swelling, dissolution or erosion (i.e., time controlled release), polymers that are degraded by enzymes (i.e., enzyme controlled release) and polymers that form firm layers that are destroyed by an increase in pressure (i.e., pressure-controlled release).

In still another embodiment, osmotic delivery systems are used for oral sustained release administration (Verma et al., Drug Dev. Ind. Pharm., 2000, 26:695-708). In a preferred embodiment, OROS® osmotic delivery systems are used for oral sustained release delivery devices (See for example, Theeuwes et al., U.S. Pat. No. 3,845,770; and Theeuwes et al, U.S. Pat. No. 3,916,899).

In yet another embodiment, a controlled-release system can be placed in proximity of the target of the compounds and/or composition of the invention, thus requiring only a fraction of the systemic dose (See, e.g., Goodson, in "Medical Applications of Controlled Release," supra, vol. 2, pp. 115-138 (1984)). Other controlled-release systems discussed in Langer, 1990, Science 249:1527-1533 may also be used.

The compounds, and/or compositions containing compound(s) of structural Formulae (I)-(XI) of the invention may be cleaved either chemically and/or enzymatically. One or more enzymes present in the stomach, intestinal lumen, intestinal tissue, blood, liver, brain or any other suitable tissue of a mammal may enzymatically cleave the compounds and/or compositions of the invention.

Compositions of the Invention

The present composition contain a therapeutically effective amount of one or more compounds of the invention, preferably in purified form, together with a suitable amount of a pharmaceutically acceptable vehicle, which so as to provide the form for proper administration to a patient. When administered to a patient, the compounds of the invention and pharmaceutically acceptable vehicles are preferably sterile. Water is preferred vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present agents, or pH buffering agents. In addition, auxiliary, stabilizing, thickening, lubricating and coloring agents may be used.

Pharmaceutical compositions comprising a compound of the invention may be manufactured by means of conventional mixing, dissolving, granulating, dragee-making levigating, and emulsifying, encapsulating, entrapping or lyophilizing process. Pharmaceutical compositions may be formulated in conventional manner using one or more physiologically acceptable carriers, diluents, excipients or auxiliaries, which facilitate processing of compounds of the invention into preparations which can be used pharmaceutically. Proper formulation is dependent upon the route of administration chosen.

The present compositions can take the form of solutions, suspensions, emulsion, tablets, pills, pellets, and capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., Grosswald et al., U.S. Pat. No. 5,698,155). Other examples of suitable pharmaceutical vehicles have been described in the art (see Remington's Pharmaceutical Sciences, Philadelphia College of Pharmacy and Science, 17$^{th}$ Edition, 1985). Preferred compositions of the invention are formulated for oral delivery, particularly for oral sustained release administration.

Compositions for oral delivery may be in the form of tablets, lozenges, aqueous or oily suspensions, granules, powders, emulsions, capsules, syrups or elixirs, for example. Orally administered compositions may contain one or more optionally agents, for example, sweetening agents such as fructose, aspartame or saccharin; flavoring agents such as peppermint, oil of wintergreen, or cherry coloring agents and preserving agents to provide a pharmaceutically palatable preparation. Moreover, where in tablet or pill form, the compositions may be coated to delay disintegration and absorption in the gastrointestinal tract, thereby providing a sustained action over an extended period of time. Selectively permeable membranes surrounding an osmotically active driving compound are also suitable for orally administered compounds of the invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

For oral liquid preparations such as, for example, suspensions, elixirs and solutions, suitable carriers, excipients or diluents include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about mM to about 50 mM) etc. Additionally, flavoring agents, preservatives, coloring agents, bile salts, acylcamitines and the like may be added.

Compositions for administration via other routes may also be contemplated. For buccal administration, the compositions may take the form of tablets, lozenzes, etc. formulated in conventional manner. Liquid drug formulations suitable for use with nebulizers and liquid spray devices and EHD aerosol devices will typically include a compound of the invention with a pharmaceutically acceptable vehicle. Preferably, the pharmaceutically acceptable vehicle is a liquid such as alcohol, water, polyethylene glycol or a perfluorocarbon. Optionally, another material may be added to alter the aerosol properties of the solution or suspension of compounds of the invention. Preferably, this material is liquid such as alcohol, glycol, polyglycol or fatty acid. Other methods of formulating liquid drug solutions or suspension suitable for use in aerosol devices are known to those of skill in the art (see, e.g., Biesalski, U.S. Pat. No. 5,112,598; Biesalski, U.S. Pat. No. 5,556,611). A compound of the invention may also be formulated in rectal or vaginal compositions such as suppositories or retention enemas, e.g., containing conventional suppository bases such as cocoa, butter or other glycerides. In addition to the formulations described previously, a compound of the invention may also be formulated as depot preparation.

Such long acting formulations may be administered by implantation (for example, subcutaneously or intramuscularly) or by intramuscular injection. Thus, for example, a compound of the invention may be formulated with suitable polymeric or hydrophobic materials (for example, as an emulsion in an acceptable oil) or ion exchange resins, or as sparingly soluble derivatives, for example, as a sparingly soluble salt.

When a compound of the invention is acidic, it may be included in any of the above-described formulations as the free acid, a pharmaceutically acceptable salt, a solvate or hydrate. Pharmaceutically acceptable salts substantially retain the activity of the free acid, may be prepared by reaction with bases and tend to be more soluble in aqueous and other protic solvents than the corresponding free acid form.

Methods of Use and Doses

A compound of the invention, or compositions thereof, will generally be used in an amount effective to achieve the intended purpose. For use to treat schizophrenia and related psychoses such as acute manic, bipolar disorder, autistic disorder and depression. The compounds of Formulae (I)-(XI) and compositions containing a compound of Formulae (I)-(XI) are administered or applied in a therapeutically effective amount.

The amount of a compound of the invention that will be effective in the treatment of a particular disorder or condition disclosed herein will depend on the nature of the disorder or condition, and can be determined by standard clinical techniques known in the art as previously described. In addition, in vitro or in vivo assays may optionally be employed to help identify optimal dosage ranges. The amount of a compound of the invention administered will, of course, is dependent on, among other factors, the subject being treated, and the weight of the subject, the severity of the affliction, the manner of administration and the judgment of the prescribing physician. For example, the dosage may be delivered in a pharmaceutical composition by a single administration, by multiple applications or controlled release. In a preferred embodiment, the compounds of the invention are delivered by oral sustained release administration. Preferably, in this embodiment, the compounds of the invention are administered twice per day, and more preferably, once per day. Dosing may be repeated intermittently, may be provided alone or in combination with other drugs and may continue as long as required for effective treatment of the disease state or disorder.

The compounds and/or compositions containing compound(s), of structural Formulae (I)-(XI) for the pharmacological treatment of schizophrenia and related psychoses such as acute maniac, bipolar disorder, autistic disorder and depression may be administered in the range 0.1 mg to 500 mg preferably 1 mg to 100 mg per day given in one or more doses and more preferably 5 mg, 10 mg, 15 mg, 20 mg, 25 mg, 35 mg or 50 mg per day and most preferably 25 mg.

The compounds of the invention are preferably assayed in vitro and in vivo, for the desired therapeutic or prophylactic activity, prior to use in humans. The compounds of the invention may also be demonstrated to be effective and safe using animal model systems.

Preferably, the therapeutically effective dose of a compound of the invention described herein will provide therapeutic benefit without causing substantial toxicity. Toxicity of compounds of the invention may be determined using standard pharmaceutical procedures and may be readily ascertained by the skilled artisan. The dose ratio between toxic and therapeutic effect is the therapeutic index. A compound of the invention will preferably exhibit particularly high therapeutic indices in treating disease and disorders. The dosage of a compound of the inventions described herein will preferably be within a range of circulating concentrations that include an effective dose with little or no toxicity.

Combination Therapy

In certain embodiments of the present invention, the compounds of the invention can be used in combination therapy with at least one other therapeutic agent. The compound of the invention and the therapeutic agent can act additively or, more preferably, synergistically. In a preferred embodiment, composition comprising a compound of the invention is administered concurrently with the administration of another therapeutic agent, which can be part of the same composition. In another embodiment, a composition comprising a compound of the invention is administered prior or subsequent to administration of another therapeutic agent.

EXAMPLES

The invention is further defined by reference to the following examples, which describe in detail preparation of compounds and compositions of the invention and assays for using compounds and compositions of the invention. It will be apparent to those skilled in the art that many modifications, both to materials and methods, may be practiced without departing from the scope of the invention.

In the examples below, the following abbreviations have the following meanings. If an abbreviation is not defined, it has its generally accepted meaning.

| | |
|---|---|
| Atm = | Atmosphere |
| DCM = | dichloromethane |
| DMAP = | 4-N,N-dimethylaminopyridine |
| DMF = | N,N-dimethylformamide |
| g = | gram |
| h = | hours |
| L = | liter |
| LC/MS = | liquid chromatography/mass spectroscopy |
| M = | molar |
| mL = | milliliter |
| mmol = | millimols |
| nM = | nanomolar |
| µM = | micromolar |
| MTBE = | methyl tert-butyl ether |
| rt = | room temperature |
| TEA = | triethylamine |
| THF = | tetrahydrofuran |
| TFA = | trifluoroacetic acid |

Example 1

6-Amino-2H-benzo[b][1,4]oxazin-3(4H)-one (2)

To a suspension of 6-nitro-2H-1,4-benzoxazin-3(4H)-one 1 (0.5 g, 0.0026 mol) and CuCl (0.77 g, 0.0078 mol) in anhydrous methanol (25 mL), stirred at 25° C. was added potassium borohydride (0.98 g, 0.018 mol) in portions (exothermic with evolution of hydrogen gas). The reaction mixture was stirred at 25° C. for 30 min. The black precipitate formed was filtered and washed with methanol. The combined filtrate and washings was evaporated to give 6-amino-2H-benzo[b][1,4]oxazin-3(4H)-one which was purified by silica gel column chromatography using ethyl acetate. Brown solid (0.29 g, 67%). $^1$H NMR (400 MHz, CDCl$_3$): δ 4.34 (s, 2H); 4.81 (s, 2H); 6.09 (dd, J=2.8, 8.4 Hz, 1H); 6.14 (d, J=2.8 Hz, 1H); 6.59 (d, J=8.4 Hz, 1H); 10.44 (s, 1H).

General procedure for Synthesis of 4a-b

A mixture of 6-amino-2H-benzo[b][1,4]oxazin-3(4H)-one 2 (0.08 g, 0.0005 mol), 4-(4-(substituted-phenyl)piperazin-1-yl)butanoic acid 3a-b (0.0005 mol), dicyclohexylcarbodiimide (0.1 g, 0.0005 mol), 4-(dimethylamino)pyridine (0.006 g, 0.00005 mol) in 10 mL dichloromethane was stirred at room temperature for overnight. The progress of the reaction was monitored by thin layer chromatography (TLC). The reaction mixture was cooled; filtered to remove the urea precipitated, washed with saturated sodium bicarbonate solution, dried over sodium sulfate and evaporated under reduced pressure to give 4-(4-(substituted-phenyl)piperazin-1-yl)-N-(3-oxo-3,4-dihydro-2H-benzo[b][1,4]oxazin-6-yl)butanamide 4a-b which was purified by silica gel column chromatography using 0-10% gradient of ethyl acetate and methanol. The pure products 4a-b gave satisfactory 1H NMR and/or Mass spectral data.

Example 2

4-(4-(2-Methoxyphenyl)piperazin-1-yl)-N-(3-oxo-3,4-dihydro-2H-benzo[b][1,4]oxazin-6-yl)butanamide (4a). White solid (0.06 g, 29%). $^1$H NMR (400 MHz, CDCl$_3$): δ 1.94-2.00 (m, 2H); 2.53-2.59 (m, 4H); 2.70 (br s, 4H); 3.14 (br s, 4H); 3.87 (s, 3H); 4.55 (s, 2H); 6.63 (dd, J=2.4, 8.8 Hz, 1H); 6.84-6.88 (m, 2H); 6.93-6.95 (m, 2H); 6.99-7.04 (m, 1H); 7.82 (d, J=2.4 Hz, 1H); 9.04 (br s, 1H); 9.12 (br s, 1H). MS (ESI): m/z=425.2 (M+H$^+$).

Example 3

4-(4-(2,3-Dichlorophenyl)piperazin-1-yl)-N-(3-oxo-3,4-dihydro-2H-benzo[b][1,4]oxazin-6-yl)butanamide (4b). White solid (0.08 g, 34%). $^1$H NMR (400 MHz, CDCl$_3$): δ 1.93-2.00 (m, 2H); 2.50-2.57 (m, 4H); 2.68 (br s, 4H); 3.09 (br s, 4H); 4.50 (s, 2H); 6.63 (dd, J=2.4, 8.8 Hz, 1H); 6.88 (d, J=8.8 Hz, 1H); 6.99-6.92 (m, 1H); 7.13-7.20 (m, 2H); 7.71-7.72 (m, 1H); 8.46 (br s, 1H); 8.58 (br s, 1H). MS (ESI): m/z=463.2 (M$^+$)

General Procedure for Synthesis of 5a-b

To a solution of 4-(4-(substituted-phenyl)piperazin-1-yl)-N-(3-oxo-3,4-dihydro-2H-benzo[b][1,4]oxazin-6-yl)butanamide 4a-b in 5 mL dichloromethane was added 2 mL 2M Hal solution in diethyl ether, and then the solution was evaporated at 25° C. to give 4-(4-(substituted-phenyl)piperazin-1-yl)-N-(3-oxo-3,4-dihydro-2H-benzo[b][1,4]oxazin-6-yl)butanamide hydrochloride 5a-b. The pure products 5a-b gave satisfactory 1 H NMR and/or Mass spectral data.

Example 4

4-(4-(2-Methoxyphenyl)piperazin-1-yl)-N-(3-oxo-3,4-dihydro-2H-benzo[b][1,4]oxazin-6-yl)butanamide hydrochloride (5a). White solid (60 mg). MS (ESI): m/z=425.2 (M−Hal).

Example 5

4-(4-(2,3-Dichlorophenyl)piperazin-1-yl)-N-(3-oxo-3,4-dihydro-2H-benzo[b][1,4]oxazin-6-yl)butanamide hydrochloride (5b). White solid (40 mg). MS (ESI): m/z=463.2 (M−Hal).

General Procedure for Synthesis of 8a-b

To a mixture of ethyl 4-bromobutanoate 6a (5.9 mL, 0.0437 mol) and 1-(substituted-phenyl)piperazine hydrochloride 7 (0.0437 mol) in 60 mL anhydrous acetonitrile at ice-bath temperature was added N,N-diisopropylethylamine (DIEA) (19 mL, 0.11 mol). The resulting mixture was refluxed for overnight (12 h). The progress of the reaction was monitored by thin layer chromatography (TLC). The reaction mixture was concentrated on rotavapor, the residue was dissolved in dichloromethane and washed with water, dried over sodium sulphate (Na$_2$SO$_4$) and evaporated under reduced pressure to give the corresponding ethyl 4-(4-(substituted-phenyl)piperazin-1-yl)butanoate 8 which was purified by silica gel chromatography using a gradient of hexane and ethyl acetate in good yields. The pure products 8a-b gave satisfactory 1H NMR and/or Mass spectral data.

Example 6

Ethyl 4-(4-(2-methoxyphenyl)piperazin-1-yl)butanoate (8a). Brown oil, 9.6 g (99%). $^1$H NMR (400 MHz, CDCl$_3$): δ 1.23 (t, J=7.2 Hz, 3H), 1.82 (quintet, J=7.2 Hz, 2H); 2.35 (t, J=7.2 Hz, 2H); 2.43 (t, J=7.2 Hz, 2H); 2.63 (broad s, 4H); 3.07 (broad s, 4H); 3.84 (s, 3H); 4.13 (q, J=7.2 Hz, 2H); 6.83-6.99 (m, 4H).

Example 7

Ethyl 4-(4-(2,3-dichlorophenyl)piperazin-1-yl)butanoate (8b). Yellow oil, 3.2 g (93%). $^1$H NMR (400 MHz, CDCl$_3$): δ 1.24 (t, J=7.2 Hz, 3H), 1.83 (quintet, J=7.2 Hz, 2H); 2.34 (t, J=7.2 Hz, 2H); 2.42 (t, J=7.2 Hz, 2H); 2.61 (broad s, 4H); 3.03 (broad s, 4H); 4.12 (q, J=7.2 Hz, 2H); 6.90-6.96 (m, 1H); 7.09-7.14 (m, 2H).

General Procedure for Synthesis of 3a-b

To a solution of ethyl 4-(4-(substituted-phenyl)piperazin-1-yl)butanoate 8 (0.006 mol) in 10 mL methanol was added 1M sodium hydroxide solution (6.5 mL, 0.006 mol). The resulting mixture was stirred at room temperature for overnight (12 h). The progress of the reaction was monitored by thin layer chromatography (TLC). The reaction mixture was concentrated to remove methanol. The residual aqueous solution pH was adjusted to 7 by adding 2M Hal solution. (3b precipitated as a white solid). The resulting solution was saturated with sodium chloride and extracted with dichloromethane (2×100 mL). The combined organic layers was dried over sodium sulphate and evaporated to give 4-(4-(substitutedphenyl)piperazin-1-yl)butanoic acid 3 which was purified by triturating with methyl tert-butyl ether. The pure products 3a-b gave satisfactory 1H NMR and/or Mass spectral data.

Example 8

4-(4-(2-Methoxyphenyl)piperazin-1-yl)butanoic acid (3a). White solid, 0.9 g (49%). $^1$H NMR (400 MHz, CDCl$_3$): δ 1.87 (quintet, J=5.6 Hz, 2H); 2.60 (t, J=5.6 Hz, 2H); 2.76 (t, J=5.6 Hz, 2H); 2.96 (broad s, 4H); 3.20 (broad s, 4H); 3.85 (s, 3H); 6.85-6.92 (m, 3H), 7.00-7.05 (m, 1H).

Example 9

4-(4-(2,3-Dichlorophenyl)piperazin-1-yl)butanoic acid (3b). White solid, 1.4 g (99%). $^1$H NMR (400 MHz, CDCl$_3$): δ 1.88 (quintet, J=5.6 Hz, 2H); 2.63 (t, J=5.6 Hz, 2H); 2.78 (t, J=5.6 Hz, 2H); 2.95 (broad s, 4H); 3.18 (broad s, 4H); 6.96 (dd, J=1.6 Hz, 7.6 Hz, 1H); 7.14-7.21 (m, 2H).

Example 10

Ethyl 2-(4-methoxy-2-nitrophenoxy)acetate (11)

A mixture of 4-methoxy-2-nitrophenol 9 (1.69 g, 0.01 mol), potassium carbonate (2.76 g, 0.02 mol) and ethyl bromoacetate 6d (1.1 mL, 0.01 mol) in 20 mL anhydrous acetone was refluxed for overnight (12 h). The progress of the reaction was monitored by thin layer chromatography. The reaction mixture was evaporated, the residue was diluted with water and the mixture was extracted with ethyl acetate. The organic layer was washed with brine, dried over sodium sulfate and evaporated to give ethyl 2-(4-methoxy-2-nitrophenoxy)acetate 11 which was purified by silica gel column chromatography using 0-50% gradient of hexane and ethyl acetate.

Yellow solid (2.18 g, 85%). $^1$H NMR (400 MHz, CDCl$_3$): δ 1.28 (t, J=7.2 Hz, 3H); 3.82 (s, 3H); 4.25 (q, J=7.2 Hz, 2H); 4.70 (s, 2H); 7.01 (d, J=9.2 Hz, 1H); 7.08 (dd, J=3.2, 9.2 Hz, 1H); 7.40 (d, J=2.8 Hz, 1H).

Example 11

Ethyl 2-(4-hydroxy-2-nitrophenoxy)acetate (12)

To a solution of ethyl 2-(4-methoxy-2-nitrophenoxy)acetate 11 (1.0 g, 0.004 mol) in 10 mL dichloromethane cooled in an ice-bath was added aluminum chloride (1.6 g, 0.0133 mol) portion wise. The resulting mixture was gradually warmed to room temperature and then refluxed for 4 h. The progress of the reaction was monitored by thin layer chromatography (TLC). The reaction mixture was washed with saturated sodium bicarbonate solution and dried over sodium sulfate to give ethyl 2-(4-hydroxy-2-nitrophenoxy)acetate 12 which was purified by silica gel column chromatography using a gradient of hexane and ethyl acetate.

White solid (0.28 g, 37%). $^1$H NMR (400 MHz, CDCl$_3$): δ 1.26 (t, J=6.8 Hz, 3H); 4.27 (q, J=6.8 Hz, 2H); 4.71 (S, 2H); 6.32 (S, 1H); 6.90 (d, J=8.8 Hz, 1H); 6.99 (dd, J=3.2 Hz; 8.8 Hz, 1H); 7.30 (d, J=2.8 Hz, 1H).

Example 12

Ethyl 2-(4-(4-bromobutoxy)-2-nitrophenoxy)acetate (14)

To a solution of ethyl 2-(4-hydroxy-2-nitrophenoxy)acetate 12 (0.17 g, 0.0007 mol) in 10 mL acetone was added potassium carbonate (0.39 g, 0.0028 mol). The reaction mixture was stirred at room temperature for 10 min. Then 1,4-dibromobutane 13 (0.33 mL, 0.0028 mol) was added. The resulting mixture was heated at reflux for 12 h. The progress of the reaction was monitored by thin layer chromatography (TLC). Acetone was evaporated and the residue was diluted with water, extracted with ethyl acetate and dried over sodium sulfate to give ethyl 2-(4-(4-bromobutoxy)-2-nitrophenoxy) acetate 14 which was purified by silica gel column chromatography using 0-20% gradient of hexane and ethyl acetate. Yellow oil (0.52 g, 92%). $^1$H NMR (400 MHz, CDCl$_3$): δ 1.26 (t, J=6.8 Hz, 3H); 1.91-1.98 (m, 2H); 2.02-2.09 (m, 2H); 3.48 (t, J=6.8 Hz, 2H); 3.99 (t, J=6.0 Hz, 2H); 4.26 (q, J=6.8 Hz, 2H); 4.70 (s, 2H); 6.99-7.02 (m, 2H); 7.38 (d, J=3.2 Hz, 1H).

Example 13

Ethyl 4-(2-(4-(4-(4-(2-ethoxy-2-oxoethoxy)-3-nitrophenoxy)butyl)piperazin-1-yl)phenoxy)-butanoate (16a)

To a solution of ethyl 2-(4-(4-bromobutoxy)-2-nitrophenoxy)acetate 14 (0.5 g, 0.0013 mol) in 40 mL acetonitrile was added DIEA (0.9 mL, 0.0052 mol) and then ethyl 4-(2-(piperazin-1)phenoxy)butanoate hydrochloride 15a (0.5g, 0.0016 mol.) in 10 mL of acetonitrile was added. The reaction mixture was stirred at reflux for 18 h. The progress of the reaction was monitored by thin layer chromatography (TLC). After the reaction was complete acetonitrile was evaporated and the residue was diluted with water, extracted with ethyl acetate and dried over anhydrous Na$_2$SO$_4$ to give ethyl 4-(2-(4-(4-4-(2-ethoxy-2-oxoethoxy)-3-nitrophenoxy)butyl)piperazin-1-yl)phenoxy)butanoate 16a which was purified by silica gel column chromatography using a gradient of hexane and ethyl acetate. Yellow oil (0.73 g, 93%). $^1$H NMR (400 MHz, CDCl$_3$): δ 1.24 (t, J=7.6 Hz, 6H); 1.69-1.72 (m, 2H); 1.81-1.83 (m, 2H); 2.12-2.16 (m, 2H); 2.47 (t, J=6.8 Hz, 2H); 2.53 (t, J=7.2 Hz, 2H); 2.64 (br s, 4H); 3.10 (br s, 4H); 3.98 (t, J=6.0 Hz, 2H); 4.03 (t, J=6.4 Hz, 2H); 4.12 (q, J=7.6 Hz, 4H); 4.70 (s, 2H); 6.82-7.07 (m, 6H); 7.38 (d, J=2.8 Hz, 1H).

Example 14

Ethyl 2-(2-(4-(4-(4-(2-ethoxy-2-oxoethoxy)-3-nitrophenoxy)butyl)piperazin-1-yl)phenoxy)-2,2-dimethylbutanoate (16b)

The compound 16b was synthesized by reacting 14 and 15b following the same protocol described for the synthesis of compound 16a. Yellow oil (0.73 g, 90%). $^1$H NMR (400 MHz, CDCl$_3$): δ 1.24 (t, J=7.6 Hz, 6H); 1.27 (s. 6H); 1.73 (br s, 2H); 1.82-1.85 (m, 2H); 2.10 (t, J=6.8 Hz, 2H); 2.49 (br s, 2H); 2.67 (br s, 4H); 3.11 (br s, 4H); 3.99-4.03 (m, 4H); 4.08-4.14 (m, 4H); 4.71 (s, 2H); 6.83-7.08 (m, 6H); 7.38 (br s, 1H).

Example 15

Ethyl 2-(2-(4-(4-(4-(2-ethoxy-2-oxoethoxy)-3-nitrophenoxy)butyl)piperazin-1-yl)phenoxy)-2-methylpropanoate (16c)

The compound 16c was synthesized by reacting 14 and 15c following the same protocol described for the synthesis of compound 16a. Yellow oil.(0.57 g, 76%). 1H NMR (400 MHz, CDCl$_3$): δ 1.24 (t, J=7.6 Hz, 6H); 1.58 (s, 6H); 1.68-1.72 (m, 2H); 1.81-1.84 (m, 2H); 2.46 (t, J=7.2 Hz, 2H); 2.62 (br s, 4H); 3.11 (br s, 4H); 3.98 (t, J=6.4 Hz, 2H); 4.24 (q, J=7.6 Hz, 4H); 4.70 (s, 2H); 6.78-7.07 (m, 6H); 7.37 (br s, 1H).

Example 16

Ethyl 4-(2-(4-(4-(3-oxo-3,4-dihydro-2H-benzo[b][1,4]oxazin-6-yloxy)butyl)piperazin-1-yl)phenoxy) butanoate (17a)

Ethyl 4-(2-(4-(4-4-(2-ethoxy-2-oxoethoxy)-3-nitrophenoxy)butyl)piperazin-1-yl)phenoxy)-butanoate 16a (0.73 g, 0.0012 mol) was dissolved in a mixture of 20 mL ethanol and 2 mL acetic acid in a 100 mL flask equipped with an efficient condenser, and the stirred mixture brought to a gentle reflux. Iron powder (0.5 g, 0.009 mol) was added, followed immediately by iron(III) chloride hexahydrate (0.05 g, 0.0002 mol). The mixture was refluxed for a further 3 h, then cooled and filtered using a Buchner funnel, washed with ethanol. The combined filtrate and washings were evaporated. To the residue was added ethyl acetate and water, and the aqueous layer was extracted twice with ethyl acetate. The combined organic layers were dried and concentrated to give ethyl 4-(2-(4-(4-(3-oxo-3,4-dihydro-2H-benzo[b][1,4]oxazin-6-yloxy)butyl) piperazin-1-yl)phenoxy)butanoate 17a which was purified by silica gel column chromatography using a gradient of hexane and ethyl acetate. Yellow oil (0.3 g, 50%). $^1$H NMR (400

MHz, CDCl₃): δ 1.25 (t, J=7.2 Hz, 3H); 1.79 (br s, 4H); 2.15 (t, J=7.2 Hz, 2H); 2.15 (t, J=7.2 Hz, 2H); 2.54 (t, J=7.2 Hz, 2H); 2.74 (br s, 4H); 3.917 (br s, 4H); 3.93 (br s, 2H); 4.04 (t, J=6.0 Hz, 2H); 4.15 (q, J=7.2 Hz, 2H); 4.54 (s, 2H); 6.34 (d, J=2.4 Hz, 1H); 6.50 (dd, J=2.8 Hz; 8.8 Hz, 1H); 6.84-6.96 (m, 5H); 8.20 (br s, 1H). MS (ESI): m/z=512.4 (M+H).

Example 17

Ethyl 2,2-dimethyl-4-(2-(4-(4-(3-oxo-3,4-dihydro-2H-benzo[b][1,4]oxazin-6-yloxy)butyl)piperazin-1-yl)phenoxy)butanoate (17b)

The compound 17b was synthesized from 16b following the same protocol described for the synthesis of compound 17a. Yellow oil (0.31 g, 51%). ¹H NMR (400 MHz, CDCl₃): δ 1.25 (t, J=7.2 Hz, 3H); 1.26 (s, 6H); 1.75 (br s, 4H); 2.09 (t, J=7.2 Hz, 2H); 2.53 (br s, 2H); 2.72 (br s, 4H); 3.12 (br s, 4H); 3.89 (br s, 2H); 4.00 (t, J=7.2 Hz, 2H); 4.12 (q, J=7.2 Hz, 2H); 4.54 (s, 2H); 6.41 (br s, 1H); 6.47 (dd d, J=2.8 Hz; 8.8 Hz, 1H); 6.83-6.94 (m, 5H); 8.20 (br s, 1H). MS (ESI): m/z=540.4 (M+H).

Example 18

Ethyl 2-methyl-2-(2-(4-(4-(3-oxo-3,4-dihydro-2H-benzo[b][1,4]oxazin-6-yloxy)butyl)piperazin-1-yl)phenoxy)propanoate (17c)

The compound 17c was synthesized from 16c following the same protocol described for the synthesis of compound 17a. Yellow oil (0.13 g, 50%). ¹H NMR (400 MHz, CDCl₃): δ 1.24 (t, J=7.6 Hz, 3H); 1.58 (s, 6H); 1.70-1.78 (m, 4H); 2.48 (t, J=7.6 Hz, 2H); 2.65 (br s, 4H); 3.12 (br s, 4H); 3.90 (t, J=6.0 Hz, 2H); 4.24 (q, J=7.6 Hz, 2H); 4.53 (s, 2H); 6.40 (d, J=2.8 Hz, 1H); 6.48 (dd, J=2.8 Hz; 8.8 Hz, 1H); 6.78-6.97 (m, 5H); 9.21 (br s, 1H). MS (ESI): m/z=512.3 (M+H).

General Procedure for Synthesis of 18a-c

To a solution of 4-(2-(4-(4-(3-oxo-3,4-dihydro-2H-benzo[b][1,4]oxazin-6-yloxy)butyl)piperazin-1-yl)phenoxy)-substituted esters 17a-c in 5 mL dichloromethane was added 2 mL 2M Hal solution in diethyl ether, and then the solution was evaporated at 25° C. to give 4-(2-(4-(4-(3-oxo-3,4-dihydro-2H-benzo[b][1,4]oxazin-6-yloxy)butyl)piperazin-1-yl)phenoxy)-substituted esters hydrochloride 18a-c. The pure products 18a-c gave satisfactory 1H NMR and/or Mass spectral data.

Example 19

Ethyl 4-(2-(4-(4-(3-oxo-3,4-dihydro-2H-benzo[b][1,4]oxazin-6-yloxy)butyl)piperazin-1-yl)phenoxy)butanoate hydrochloride (18a). White solid (0.30 g, 100%). MS (ESI): m/z=512.4 (M−Hal).

Example 20

Ethyl 2,2-dimethyl-4-(2-(4-(4-(3-oxo-3,4-dihydro-2H-benzo[b][1,4]oxazin-6-yloxy)butyl)piperazin-1-yl)phenoxy)butanoate hydrochloride (18b). White solid (0.30 g, 100%). MS (ESI): m/z=540.4 (M−Hal).

Example 21

Ethyl 2-methyl-2-(2-(4-(4-(3-oxo-3,4-dihydro-2H-benzo[b][1,4]oxazin-6-yloxy)butyl)piperazin-1-yl)phenoxy)propanoate hydrochloride (18c). White solid (0.13 g, 100%). MS (ESI): m/z=512.3 (M−Hal).

Example 22 tert-Butyl 4-(2-hydroxyphenyl)piperazine-1-carboxylate (20)

To a stirred suspension of 1-(2-hydroxyphenyl)piperazine 19 (1.78 g, 0.01 mol) in 20 mL tetrahydrofuran (in a round bottom flask fitted with a gas bubbler) was added a solution of di-tert-butylcarbonate (2.62 g, 0.012 mol) in 10 mL tetrahydrofuran at room temperature. Soon it became a clear solution and a gas was evolved. The resulting mixture was heated at 60° C. for 6 h. The progress of the reaction was monitored by thin layer chromatography (TLC). The solvent was evaporated, the residue was dissolved in 100 mL ethyl acetate and washed with 100 mL water, dried over sodium sulphate (Na₂SO₄) and evaporated to give tert-Butyl 4-(2-hydroxyphenyl)piperazine-1-carboxylate 20 which was purified by triturating with hexanes. White solid, 2.5 g (92%). ¹H NMR (400 MHz, CDCl₃): δ 1.49 (s, 9H); 2.81 (t, J=4.8 Hz, 4H); 3.58 (t, J=4.8 Hz, 4H); 6.84-6.88 (m, 1H); 6.94-6.99 (m, 1H); 7.06-7.12 (m, 2H).

Example 23 tert-butyl 4-(2-(4-ethoxy-4-oxobutoxy)phenyl)piperazine-1-carboxylate (21a)

To a stirred solution of tert-butyl 4-(2-hydroxyphenyl)piperazine 20 (1 g, 0.0035 mol.) and cesium carbonate (2.34 g, 0.0071 mol.) in 5 mL of DMF anhydrous was added a solution of ethyl 4-bromobutanoate (6a) at rt. The resulting mixture was heated at 70° C. overnight (12 h). The progress of the reaction was monitored by thin layer chromatography (TLC). After the reaction was complete, the reaction mixture was diluted with 25 mL of ethyl acetate and filtered to remove cesium carbonate. The filtrate was washed with saturated aqueous NaHCO₃ solution, dried over Na₂SO₄ and evaporated to give tert-butyl 4-(2-(4-ethoxy-4-oxobutoxy)phenyl)piperazine-1carboxylate 21a which was purified by silica gel chromatography using a gradient elution of ethyl acetate and hexane. Colorless oil (1.1 g, 78%). ¹H NMR (400 MHz, CDCl₃): δ 1.25 (t, J=6.4 Hz, 3H); 1.45 (s, 9H); 2.14 (q, J=7.2 Hz, 2H); 2.53 (t, J=7.2Hz, 2H); 3.00 (br s, 4H); 3.58 (br s, 4H); 4.04 (t, J=6.4 Hz, 2H); 4.12 (q, J=6.4 Hz, 2H); 6.84-6.97 (m, 4H).

Example 24 tert-butyl 4-(2-(4-ethoxy-3,3-dimethyl-4oxobutoxy)phenyl)piperazine-1-carboxylate (21b)

The compound 21b was synthesized by reacting 20 and 6b following the same protocol described for the synthesis of compound 21a. Colorless oil (0.81 g, 55%).¹H NMR (400 MHz, CDCl₃): δ 1.26 (t, J=6.8 Hz, 3H); 1.27 (s, 6H); 1.47 (s, 9H); 2.12 (t, J=7.2 Hz, 2H); 2.99 (br s, 4H); 3.58 (br s, 4H); 4.02 (t, J=6.4 Hz, 2H); 4.13 (q, J=6.8 Hz, 2H); 6.84-6.97 (m, 4H).

Example 25 tert-butyl 4-(2-(1-ethoxy-2-methyl-1-oxopropan-2-yloxy)phenyl)piperazine-1-carboxylate (21c)

The compound 21c was synthesized by reacting 20 and 6c following the same protocol described for the synthesis of compound 21a. Colorless oil (0.92 g, 67%). ¹H NMR (400

MHz, CDCl$_3$): δ 1.26 (t, J=6.8 Hz, 3H); 1.42 (s, 9H); 1.59 (s, 6H); 3.01 (br s, 4H); 3.56 (br s, 4H); 4.10 (q, J=6.8Hz, 2H); 6.78-6.96 (m, 4H).

General Procedure for Synthesis of 15a-c

To a stirred solution of compounds 21a-c (0.0028 mol) in 5 mL DCM at 0° C. was added a solution of 5 mL of TFA. The resulting mixture was stirred from 0° C. to rt. The progress of the reaction was monitored by thin layer chromatography (TLC). After the reaction was complete the solvents (TFA and DCM) were evaporated to give the corresponding trifluoroacetic acid salts 15a-c. The compounds 15a-c were used in the synthesis of compounds 16a-c without any further purification.

General Procedure for Synthesis of 23a-b

A mixture of 6-acetyl-2H-1,4-benzoxazin-3($^4$H)-one 22 (1.0 g, 0.005 mol), potassium carbonate (1.38 g, 0.01 mol) and ester 6a (0.01 mol) in 10 mL anhydrous acetone was refluxed for overnight (12 h). The progress of the reaction was monitored by thin layer chromatography. The reaction mixture was evaporated, the residue was diluted with water and the mixture was extracted with ethyl acetate. The organic layer was washed with brine, dried over sodium sulfate and evaporated to give ethyl 4-(6-acetyl-3-oxo-2H-benzo[b][1,4]oxazin-4(3H)-yl)alkanoate 23a-b which was purified by silica gel column chromatography using 0-50% gradient of hexane and ethyl acetate. The pure products 23a-b gave satisfactory 1H NMR and/or Mass spectral data.

Example 26

Ethyl 4-(6-acetyl-3-oxo-2H-benzo[b][1,4]oxazin-4(3H)-yl)butanoate (23a). White solid (1.33 g, 83%). $^1$H NMR (400 MHz, CDCl$_3$): δ 1.27 (t, J=7.2 Hz, 3H); 2.01 (quintet, J=6.4 Hz, 2H); 2.44 (t, J=7.2 Hz, 2H); 2.62 (s, 3H); 4.06 (t, J=7.2 Hz, 2H); 4.17 (q, J=7.2 Hz, 2H); 4.67 (s, 2H); 7.02-7.05 (m, 1H); 7.63-7.66 (m, 1H); 7.83-7.84 (m, 1H).

Example 27

Ethyl 2-(6-acetyl-3-oxo-2H-benzo[b][1,4]oxazin-4(3H)-yl)acetate (23b). The compound 23b was synthesized by reacting 22 and 6d following the same protocol described for the synthesis of compound 23a. White solid (0.47 g, 32%). $^1$H NMR (400 MHz, CDCl$_3$): δ 1.30 (t, J=7.2 Hz, 3H); 2.55 (s, 3H); 4.25 (q, J=7.2 Hz, 2H); 4.70 (s, 2H); 4.74 (s, 2H); 7.05 (dd, J=1.6, 8.4 Hz, 1H); 7.41-7.42 (m, 1H); 7.60-7.63 (m, 1H).

General Procedure for Synthesis of 24a-b

To a stirred suspension of urea hydrogen peroxide (0.85 g, 0.009 mol) and sodium bicarbonate (0.76 g, 0.009 mol) in anhydrous dichloromethane (10 mL) under nitrogen atmosphere at ice-bath temperature was added ethyl 4-(6-acetyl-3-oxo-2H-benzo[b][1,4]oxazin-4(3H)-yl)alkanoate 23a-b (0.003 mol). After stirring for 10 min trifluoroacetic anhydride (0.8 mL, 0.006 mol) was added drop-wise into the reaction mixture. The reaction mixture was stirred at ice-bath temperature for 1 h and then at room temperature for 24 h. The progress of the reaction was monitored by thin layer chromatography (TLC). The reaction mixture was diluted with 20 mL dichloromethane and washed successively with water (2×20 mL), dried over sodium sulfate and evaporated under reduced pressure at room temperature to give ethyl 4-(6-acetoxy-3-oxo-2H-benzo[b][1,4]oxazin-4(3H)-yl)alkanoate 24a-b which was purified by silica gel column chromatography using 0-50% gradient of hexane and ethyl acetate. The pure products 24a-b gave satisfactory 1H NMR and/or Mass spectral data.

Example 28

Ethyl 4-(6-acetoxy-3-oxo-2H-benzo[b][1,4]oxazin-4(3H)-yl)butanoate (24a). Colorless oil (1.39 g, 100%). $^1$H NMR (400 MHz, CDCl$_3$): δ 1.26 (t, J=7.2 Hz, 3H); 1.99 (quintet, J=6.8 Hz, 2H); 2.30 (s, 3H); 2.40 (t, J=7.2 Hz, 2H); 3.93 (t, J=7.6 Hz, 2H); 4.14 (q, J=7.2 Hz, 2H); 4.58 (s, 2H); 6.70-6.73 (m, 1H); 6.88 (d, J=2.4 Hz, 1H); 6.97 (dd, J=0.8, 8.8 Hz, 1H).

Example 29

Ethyl 2-(6-acetoxy-3-oxo-2H-benzo[b][1,4]oxazin-4(3H)-yl)acetate (24b). Colorless oil (0.47 g, 95%). $^1$H NMR (400 MHz, CDCl$_3$): δ 1.27 (t, J=7.2 Hz, 3H); 2.28 (s, 3H); 4.24 (q, J=J=7.2 Hz, 2H); 4.60 (s, 2H); 4.66 (s, 2H); 6.51-6.52 (m, 1H); 6.72-6.76 (m, 1H); 7.00 (dd, J=1.6, 8.8 Hz, 1H).

General Procedure for Synthesis of 25a-b

Morpholine (0.42 mL, 0.0048 mol) was added to a solution of ethyl 2-(6-acetoxy-3-oxo-2H-benzo[b][1,4]oxazin-4(3H)-yl)alkanoate 24 (0.0016 mol) in 10 mL THF and the resulting mixture was refluxed for 1 h. The progress of the reaction was monitored by thin layer chromatography (TLC). The reaction mixture was evaporated, diluted with ethyl acetate, washed with brine (2×100 mL), dried over sodium sulfate and evaporated under reduced pressure to give ethyl 2-(6-hydroxy-3-oxo-2H-benzo[b][1,4]oxazin-4(3H)-yl)alkanoate 25a-b. The pure products 25a-b gave satisfactory 1 H NMR and/or Mass spectral data.

Example 30

Ethyl 4-(6-hydroxy-3-oxo-2H-benzo[b][1,4]oxazin-4(3H)-yl)butanoate (25a). Brown oil (1.2 g, 99%). $^1$H NMR (400 MHz, CDCl$_3$): δ 1.26 (t, J=7.2 Hz, 3H); 1.98 (quintet, J=7.6 Hz, 2H); 2.42 (t, J=6.8 Hz, 2H); 3.91 (t, J=7.6 Hz, 2H); 4.14 (q, J=7.2 Hz, 2H); 4.55 (s, 2H); 6.10 (br s, 1H); 6.47 (dd, J=2.8, 8.8 Hz, 1H); 6.72 (d, J=2.4 Hz, 1H); 6.83 (d, J=8.8 Hz, 1H).

Example 31

Ethyl 2-(6-hydroxy-3-oxo-2H-benzo[b][1,4]oxazin-4(3H)-yl)acetate (25b). Red oil (0.39 g, 97%). $^1$H NMR (400 MHz, CDCl$_3$): δ 1.26 (t, J=7.2 Hz, 3H); 4.24 (q, J=7.2 Hz, 2H); 4.51 (s, 2H); 4.60 (s, 2H); 6.27-6.28 (m, 1H); 6.42-6.45 (m, 6.84 (dd, J=0.8, 8.8 Hz, 1H).

General Procedure for Synthesis of 26a-b

To a solution of ethyl 4-(6-hydroxy-3-oxo-2H-benzo[b][1,4]oxazin-4(3H)-yl)alkanoate 25a-b (0.004 mol) in 60 mL acetone was added potassium carbonate (1.7 g, 0.012 mol). The reaction mixture was stirred at room temperature for 10 min. Then 1,4-dibromobutane 13 (1.5 mL, 0.012 mol) was added. The resulting mixture was heated at reflux for 12 h. The progress of the reaction was monitored by thin layer chromatography (TLC). Acetone was evaporated and the residue was diluted with water, extracted with ethyl acetate (3×10 mL). The combined organic extracts were washed with brine and dried over sodium sulfate to give ethyl 4-(6-(4-bromobutoxy)-3-oxo-2H-benzo[b][1,4]oxazin-4(3H)-yl)alkanoate 26a-b which was purified by silica gel column chromatography using a gradient of hexane and ethyl acetate. The pure products 26a-b gave satisfactory 1lH NMR and/or Mass spectral data.

Example 32

Ethyl 4-(6-(4-bromobutoxy)-3-oxo-2H-benzo[b][1,4]oxazin-4(3H)-yl)butanoate (26a). Colorless oil (0.9 g, 51%). $^1$H NMR (400 MHz, CDCl$_3$): δ 1.26 (t, J=7.2 Hz, 3H); 1.90-2.11 (m, 6H); 2.41 (t, J=6.8 Hz, 2H); 3.49 (t, J=6.8 Hz, 2H); 3.93 (t, J=8.0 Hz, 2H); 4.00 (t, J=6.0 Hz, 2H); 4.10 (q, J=7.2 Hz, 2H); 4.53 (s, 2H); 6.50 (dd, J=2.8, 8.8 Hz, 1H); 6.78 (d, J=2.4 Hz, 1H); 6.88 (d, J=8.8 Hz, 1H).

Example 33

Ethyl 2-(6-(4-bromobutoxy)-3-oxo-2H-benzo[b][1,4]oxazin-4(3H)-yl)acetate (26b). Colorless oil (0.35 g, 58%). $^1$H NMR (400 MHz, CDCl$_3$): δ 1.26 (t, J=7.2 Hz, 3H); 1.86-1.93 (m, 2H); 1.99-2.04 (m, 2H); 3.46 (t, J=6.4 Hz, 2H); 3.91 (t, J=6.0 Hz, 2H); 4.22 (q, J=7.2 Hz, 2H); 4.59 (s, 2H); 4.60 (s, 2H); 6.30-6.31 (m, 1H); 6.47-6.51 (m, 1H); 6.90 (dd, J=2.0, 8.8 Hz, 1H).

General Procedure for Synthesis of 27a-c

A mixture of ethyl 4-(6-(4-bromobutoxy)-3-oxo-2H-benzo[b][1,4]oxazin-4(3H)-yl)alkanoate 26a-b (0.001 mol), 1-(substituted-phenyl)-piperazine hydrochloride 7 (0.25 g, 0.001 mol), N,N-diisopropylethylamine (0.5 mL, 0.003 mol) in 10 mL acetonitrile was heated at 60° C. for 12 h. The progress of the reaction was monitored by thin layer chromatography (TLC). The reaction mixture was evaporated to remove the volatiles and the residue was diluted with water, extracted with ethyl acetate, the organic extracts were washed with saturated sodium bicarbonate solution, brine and dried over sodium sulfate to give ethyl 4-(6-(4-(4-(substituted-phenyl)piperazin-1-yl)butoxy)-3-oxo-2H-benzo[b][1,4]oxazin-4(3H)-yl)alkanoate 27a-c which was purified by silica gel column chromatography using a gradient of hexane and ethyl acetate. The pure products 27a-b gave satisfactory 1H NMR and/or Mass spectral data.

Example 34

Ethyl 4-(6-(4-(4-(2-methoxyphenyl)piperazin-1-yl)butoxy)-3-oxo-2H-benzo[b][1,4]oxazin-4(3H)-yl)butanoate (27a). Colorless oil (0.22 g, 38%). $^1$H NMR (400 MHz, CDCl$_3$): δ 1.24 (t, J=7.2 Hz, 3H); 1.68-1.74 (m, 2H); 1.77-1.84 (m, 2H); 1.97 (quintet, J=8.0 Hz, 2H); 2.39 (t, J=6.8 Hz, 2H); 2.46 (t, J=7.6 Hz, 2H); 2.65 (br s, 4H); 3.08 (br s, 4H); 3.83 (s, 3H); 3.92 (t, J=7.6 Hz, 2H); 3.97 (t, J=6.8 Hz, 2H); 4.11 (q, J=7.2 Hz, 2H); 4.50 (s, 2H); 6.49 (dd, J=2.4, 8.8 Hz, 1H); 6.73 (d, J=2.4 Hz, 1H); 6.82-6.99 (m, 5H). MS (ESI): m/z=526.3 (M$^-$+H).

Example 35

Ethyl 4-(6-(4-(4-(2,3-dichlorophenyl)piperazin-1-yl)butoxy)-3-oxo-2H-benzo[b][1,4]oxazin-4(3H)-yl)butanoate (27b). Colorless oil (0.22 g, 38%). $^1$H NMR (400 MHz, CDCl$_3$): δ 1.25 (t, J=7.2 Hz, 3H); 1.70-1.75 (m, 2H); 1.80-1.85 (m, 2H); 2.01 (quintet, J=7.2 Hz, 2H); 2.41 (t, J=6.8 Hz, 2H); 2.49 (t, J=7.6 Hz, 2H); 2.66 (br s, 4H); 3.07 (br s, 4H); 3.94 (t, J=7.6 Hz, 2H); 3.99 (t, J=6.4 Hz, 2H); 4.12 (q, J=7.2 Hz, 2H); 4.50 (s, 2H); 6.51 (dd, J=2.8, 8.8 Hz, 1H); 6.74 (d, J=2.8 Hz, 1H); 6.88 (d, J=8.8 Hz, 1H); 6.95 (dd, J=2.8, 6.4 Hz, 1H); 7.11-7.16 (m, 2H). MS (ESI): m/z=564.3 (M$^+$).

Example 36

Ethyl 2-(6-(4-(4-(2,3-dichlorophenyl)piperazin-1-yl)butoxy)-3-oxo-2H-benzo[b][1,4]oxazin-4(3H)-yl)acetate (27c). Brown solid (0.4 g, 83%). $^1$H NMR (400 MHz, CDCl$_3$): δ 1.24 (t, J=7.2 Hz, 3H); 1.67-1.71 (m, 2H); 1.76-1.81 (m, 2H); 2.46 (t, J=7.2 Hz, 2H); 2.63 (br s, 4H); 3.05 (br s, 4H); 3.91 (t, J=6.0 Hz, 2H); 4.23 (q, J=7.2 Hz, 2H); 4.59 (s, 2H); 4.60 (s, 2H); 6.31 (d, J=2.4 Hz, 1H); 6.50 (dd, J=2.8, 8.8 Hz, 1H); 6.89-6.95 (m, 2H); 7.12-7.14 (m, 2H). MS (ESI): m/z=536.2 (M$^+$).

General Procedure for Synthesis of 28a-c

To a solution of 4-(6-(4-(4-(substituted-phenyl)piperazin-1-yl)butoxy)-3-oxo-2H-benzo[b][1,4]oxazin-4(3H)-yl)alkanoate 27 in 5 mL dichloromethane was added 2 mL 2M Hal solution in diethyl ether, and then the solution was evaporated at 25° C. to give 4-(6-(4-(4-(substituted-phenyl)piperazin-1-yl)butoxy)-3-oxo-2H-benzo[b][1,4]oxazin-4(3H)-yl)alkanoate hydrochloride 28a. The pure products 28a-c gave satisfactory 1H NMR and/or Mass spectral data.

Example 37

Ethyl 4-(6-(4-(4-(2-methoxyphenyl)piperazin-1-yl)butoxy)-3-oxo-2H-benzo[b][1,4]oxazin-4(3H)-yl)butanoate hydrochloride (28a). White solid (0.17 g, 100%). MS (ESI): m/z=526.3 (M−Hal).

Example 38

Ethyl 4-(6-(4-(4-(2,3-dichlorophenyl)piperazin-1-yl)butoxy)-3-oxo-2H-benzo[b][1,4]oxazin-4(3H)-yl)butanoate hydrochloride (28b). White solid (0.17 g, 100%). MS (ESI): m/z=564.3 (M−Hal).

Example 39

Ethyl 2-(6-(4-(4-(2,3-dichlorophenyl)piperazin-1-yl)butoxy)-3-oxo-2H-benzo[b][1,4]oxazin-4(3H)-yl)acetate hydrochloride (28c). White solid (0.4 g, 100%). MS (ESI): m/z=536.2 (M−Hal).

Example 40

In Vitro Pharmacology Results

The piperazine derivatives comprising Formulae (I)-(X) described in this invention were tested in the in vitro pharmacological assays to evaluate their activities for dopamine, $D_{2S}$, serotonin, 5-HT$_{1A}$ and serotonin, 5-HT$_{2A}$ receptors. The in vitro assay protocols and literature references are described herein.

Dopamine, $D_{2S}$ (human recombinant) binding assay:
Materials and Methods:

| Receptor Source: | Human recombinant expressed in CHO cells |
|---|---|
| Radioligand: | [$^3$H]Spiperone (20-60 Ci/mmol) |
| Control Compound: | Haloperidol |

Incubation Conditions:

The reactions were carried out in 50 mM TRIS-Hal (pH 7.4) containing 120 mM NaCl, 5 mM KCl, 5 mM MgCl$_2$, 1 mM EDTA for 60 minutes at 25 C. The reaction was terminated by rapid vacuum filtration onto glass fiber filters. Radioactivity trapped onto the filters was determined and compared to control values in order to ascertain any interactions of test compounds with the cloned dopamine—D₂ short binding site (Literature Reference: Jarvis, K. R. et al. Journal of Receptor Research 1993, 13(1-4), 573-590; Gundlach, A. L. et al. Life Sciences 1984, 35, 1981-1988.)

Serotonin, $5HT_{1A}$ (human recombinant) binding assay:
Materials and Methods:

| Receptor Source: | Human recombinant expressed in HEK-293 cells |
|---|---|
| Radioligand: | [³H]-8-OH-DPAT (221 Ci/mmol) |
| Control Compound: | 8-OH-DPAT |

Incubation Conditions:

The reactions were carried out in 50 mM TRIS-Hal (pH 7.4) containing 10 mM MgSO₄, 0.5 mM EDTA and 0.1% Ascorbic acid at room temperature for 1 hour. The reaction was terminated by rapid vacuum filtration onto glass fiber filters. Radioactivity trapped onto the filters was determined and compared to control values in order to ascertain any interactions of test compounds with the cloned serotonin—$5HT_{1A}$ binding site (Literature Reference: Hoyer, D. et al. Eur. Journal Pharmacol. 1985, 118, 13-23; Schoeffier, P. and Hoyer, D. Naunyn-Schmiedeberg's Arch. Pharmac. 1989, 340, 135-138)

Serotonin, $5HT_{2A}$ (human) binding assay:
Materials and Methods:
Receptor Source: Human Cortex
Radioligand: [³H]-Ketanserin (60-90 Ci/mmol)
Control Compound: Ketanserin
Incubation Conditions:

The reactions were carried out in 50 mM TRIS-Hal (pH 7.6) at room temperature for 90 minutes. The reaction was terminated by rapid vacuum filtration onto glass fiber filters. Radioactivity trapped onto the filters was determined and compared to control values in order to ascertain any interactions of test compounds with the serotonin—$5HT_{2A}$ binding site (Literature Reference: Leysen, J. E. et al. Mol. Pharmacol. 1982, 21, 301-314; Martin, G. R. and Humphrey, P. P. A. Neuropharmacol. 1994, 33(3/4), 261-273.)

The radioligand binding assays for dopamine-$D_{2S}$, serotonin-$5HT_{1A}$ and serotonin-$5HT_{2A}$ were carried out at six different concentrations and the test concentrations were 0.5 nM, 1 nM, 10 nm, 100 nM, 300 nM and 1000 nM.

The in vitro pharmacological activities of the selected compounds using radioligand binding assays are reported in the following table.

| Compound | Assay | IC50 | Ki |
|---|---|---|---|
| 5b (Example 5) | D2S | 7.89 nM | 2.89 nM |
| 5b (Example 5) | 5-HT1A | 18.50 nM | 11.40 nM |
| 5b (Example 5) | 5-HT2A | 110 nM | 57.40 nM |
| 18a (Example 19) | D2S | 19.20 nM | 6.77 nM |
| 18a (Example 19) | 5-HT1A | 16.70 nM | 10.20 nM |
| 18a (Example 19) | 5-HT2A | 572 nM | 282 nM |
| 18b (Example 20) | D2S | 147 nM | 50.20 nM |
| 18b (Example 20) | 5-HT1A | 5.44 nM | 3.30 nM |
| 18b (Example 20) | 5-HT2A | 622 nM | 340 nM |
| 18c (Example 21) | D2S | 5.93 nM | 2.09 nM |
| 18c (Example 21) | 5-HT1A | 4.41 nM | 2.67 nM |
| 18c (Example 21) | 5-HT2A | 376 nM | 185 nM |
| 28c (Example 39) | D2S | 49.40 nM | 15.50 nM |
| 28c (Example 39) | 5-HT1A | 4.45 nM | 2.96 nM |
| 28c (Example 39) | 5-HT2A | 237 nM | 106 nM |

While the invention has been particularly shown and described with reference to a preferred embodiment and various alternate embodiments, it will be understood by persons skilled in the relevant art that various changes in form and details can be made therein without departing from the spirit and scope of the invention. All printed patents and publications referred to in this application are hereby incorporated herein in their entirety by this reference.

What is claimed is:
1. A compound of structural Formula (II):

Formula II

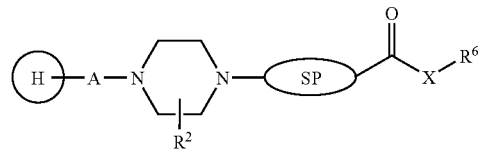

or racemic mixtures thereof, diasteromeric mixtures thereof, optical isomers thereof, isotopes thereof, or a pharmaceutically acceptable salt thereof, wherein:

X is O, S, NH or $NR^7$;

SP is a spacer, wherein the spacer is O, alkyl, substituted alkyl, alkoxy, alkylthio, or -aryl-O-alkyl-;

'A' is —O—(CH₂)ₙ—, —S—(CH₂)ₙ—, —S(O)(O)—(CH₂)ₙ—, —NH—(CH₂)ₙ—, —CH₂—O—(CH₂)ₙ—, —(CH₂)ₙ—O—CH₂—CH₂—, —CH₂—S—(CH₂)ₙ—, —(CH₂)ₙ—S—CH₂—CH₂—, —CH₂—S(O)(O)—(CH₂)ₙ—, —(CH₂)ₙ—S(O)(O)—CH₂—CH₂—, —O—C(O)—(CH₂)ₙ—, —S—C(O)—(CH₂)ₙ—, —NH—C(O)—(CH₂)ₙ—, —CH₂—C(O)—O—(CH₂)ₙ—, —CH₂—C(O)—NH—(CH₂)ₙ—, —CH₂—C(O)—S—(CH₂)ₙ—, —(CH₂)ₙ—C(O)—O—CH₂—CH₂—, —(CH₂)ₙ—C(O)—NH—CH₂—CH₂—, —(CH₂)ₙ—C(O)—S—CH₂—CH₂—, —CH₂—O—C(O)—(CH₂)ₙ—, —CH₂—NH—C(O)—(CH₂)ₙ—, —CH₂—S—C(O)—(CH₂)ₙ—, —(CH₂)ₙ—O—C(O)—CH₂—CH₂—, —(CH₂)ₙ—NH—C(O)—CH₂—CH₂—, or —(CH₂)ₙ—S—C(O)—CH₂—CH₂—;

n is an integer between 1 and 7;

cyclic ring-'H' is

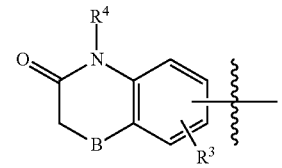

'B' is O;

$R^2$, $R^3$, and $R^4$ are independently selected from the group consisting of hydrogen, alkyl, substituted alkyl, aryl, substituted aryl, arylalkyl, substituted arylalkyl, cycloalkyl, substituted cycloalkyl, alkoxy, alkylsulfinyl, alkylsulfonyl, alkylthio, amino, alkylamino, arylalkylamino, dialkylamino, arylalkoxy, cyano, halogen, and hydroxy;

$R^6$ is alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, or substituted heteroarylalkyl;

$R^7$ is alkyl or substituted alkyl; optionally one or more hydrogens of $R^2$, $R^3$, $R^4$, $R^6$ and A are substituted with $^2H$ (deuterium).

2. The compound of claim 1, wherein the spacer is O.

3. A compound of structural Formula (III):

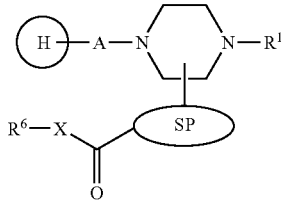

Formula III or racemic mixtures thereof, diasteromeric mixtures thereof, optical isomers thereof, isotopes thereof, or a pharmaceutically acceptable salt thereof, wherein:

X is O, S, NH or $NR^7$;

SP is a spacer, wherein the spacer is O, alkyl, substituted alkyl, alkoxy, alkylthio, or-aryl-O-alkyl-;

'A' is —O—$(CH_2)_n$—, —S—$(CH_2)_n$—, —S(O)(O)—$(CH_2)_n$—, —NH—$(CH_2)_n$—, —$CH_2$—O—$(CH_2)_n$—, —$(CH_2)_n$—O—$CH_2$—$CH_2$—, —$CH_2$—S—$(CH_2)_n$—, —$(CH_2)_n$—S—$CH_2$—$CH_2$—, —$CH_2$—S(O)(O)—$(CH_2)_n$—, —$(CH_2)_n$—S(O)(O)—$CH_2$—$CH_2$—, —O—C(O)—$(CH_2)_n$—, —S—C(O)—$(CH_2)_n$—, —NH—C(O)—$(CH_2)_n$—, —$CH_2$—C(O)—O—$(CH_2)_n$—, —$CH_2$—C(O)—NH—$(CH_2)_n$—, —$CH_2$—C(O)—S—$(CH_2)_n$—, —$(CH_2)_n$—C(O)—O—$CH_2$—$CH_2$—, —$(CH_2)_n$—C(O)—NH—$CH_2$—$CH_2$—, —$(CH_2)_n$—C(O)—S—$CH_2$—$CH_2$—, —$CH_2$—O—C(O)—$(CH_2)_n$—, —$CH_2$—NH—C(O)—$(CH_2)_n$—, —$CH_2$—S—C(O)—$(CH_2)_n$—, —$(CH_2)_n$—O—C(O)—$CH_2$—$CH_2$—, —$(CH_2)_n$—NH—C(O)—$CH_2$—$CH_2$—, or —$(CH_2)_n$—S—C(O)—$CH_2$—$CH_2$—;

n is an integer between 1 and 7;

cyclic ring-'H' is

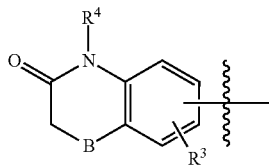

'B' is O;

$R^1$, $R^3$, and $R^4$ are independently selected from the group consisting of hydrogen, alkyl, substituted alkyl, aryl, substituted aryl, arylalkyl, substituted arylalkyl, cycloalkyl, substituted cycloalkyl, alkoxy, alkylsulfinyl, alkylsulfonyl, alkylthio, amino, alkylamino, arylalkylamino, dialkylamino, arylalkoxy, cyano, halogen, and hydroxy;

$R^6$ is alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, or substituted heteroarylalkyl;

$R^7$ is alkyl or substituted alkyl;

optionally one or more hydrogens of $R^1$, $R^3$, $R^4$, $R^6$ and A are substituted with $^2H$ (deuterium).

4. A compound of structural Formula (IV):

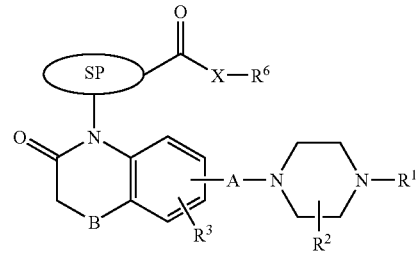

Formula IV or racemic mixtures, diasteromeric mixtures thereof, optical isomers thereof, isotopes thereof, or a pharmaceutically acceptable salt thereof, wherein:

X is O, S, NH or $NR^7$;

SP is a spacer, wherein the spacer is O, alkyl, substituted alkyl, alkoxy, alkylthio, or aryl-O-alkyl-;

'A' is —O—$(CH_2)_n$—, —S—$(CH_2)_n$—, —S(O)(O)—$(CH_2)_n$—, —NH—$(CH_2)_n$—, —$CH_2$—O—$(CH_2)_n$—, —$(CH_2)_n$—O—$CH_2$—$CH_2$—, —$CH_2$—S—$(CH_2)_n$—, —$(CH_2)_n$—S—$CH_2$—$CH_2$—, —$CH_2$—S(O)(O)—$(CH_2)_n$—, —$(CH_2)_n$—S(O)(O)—$CH_2$—$CH_2$—, —O—C(O)—$(CH_2)_n$—, —S—C(O)—$(CH_2)_n$—, —NH—C(O)—$(CH_2)_n$—, —$CH_2$—C(O)—O—$(CH_2)_n$—, —$CH_2$—C(O)—NH—$(CH_2)_n$—, —$CH_2$—C(O)—S—$(CH_2)_n$—, —$(CH_2)_n$—C(O)—O—$CH_2$—$CH_2$—, —$(CH_2)_n$—C(O)—NH—$CH_2$—$CH_2$—, —$(CH_2)_n$—C(O)—S—$CH_2$—$CH_2$—, —$CH_2$—O—C(O)—$(CH_2)_n$—, —$CH_2$—NH—C(O)—$(CH_2)_n$—, —$CH_2$—S—C(O)—$(CH_2)_n$—, —$(CH_2)_n$—O—C(O)—$CH_2$—$CH_2$—, —$(CH_2)_n$—NH—C(O)—$CH_2$—$CH_2$—, or —$(CH_2)_n$—S—C(O)—$CH_2$—$CH_2$—;

n is an integer between 1 and 7;

'B' is O;

$R^1$, $R^2$, and $R^3$ are independently selected from the group consisting of hydrogen, alkyl, substituted alkyl, aryl, substituted aryl, arylalkyl, substituted arylalkyl, cycloalkyl, substituted cycloalkyl, alkoxy, alkylsulfinyl, alkylsulfonyl, alkylthio, amino, alkylamino, arylalkylamino, dialkylamino, arylalkoxy, cyano, halogen, and hydroxy;

$R^6$ is alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, or substituted heteroarylalkyl;

$R^7$ is alkyl or substituted alkyl;

optionally one or more hydrogens of $R^1$, $R^2$, $R^3$, $R^6$ and A are substituted with $^2H$ (deuterium).

5. The compound of claim 1, having a structure of Formula (VII):

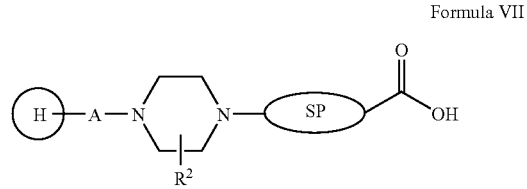

Formula VII or racemic mixtures thereof, diasteromeric mixtures thereof, optical isomers thereof, isotopes thereof, or a pharmaceutically acceptable salt thereof.

6. The compound of claim 3, having a structure of Formula (VIII):

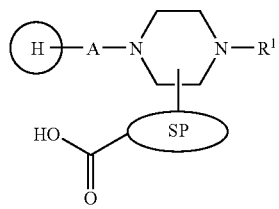

Formula VIII or racemic mixtures, diasteromeric mixtures thereof, optical isomers thereof, isotopes thereof, or a pharmaceutically acceptable salt thereof.

7. The compound of claim 4, having a structure of Formula (IX):

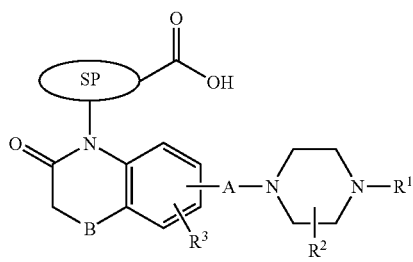

Formula IX or racemic mixtures, diasteromeric mixtures thereof, optical isomers thereof, isotopes thereof, or a pharmaceutically acceptable salt thereof.

8. The compound of claim 1, wherein the spacer is alkyl or substituted alkyl.

9. The compound of claim 1, wherein the spacer is -aryl-O-alkyl-.

10. The compound of claim 9, wherein the spacer is -phenyl-O-alkyl-.

11. The compound of claim 1, wherein X is O.

12. The compound of claim 3, wherein A is —O—(CH$_2$)$_n$—, wherein n is an integer from 1 to 7.

13. The compound of claim 1, wherein A is —O—(CH$_2$)$_n$—, wherein n is an integer from 1 to 7.

14. The compound of claim 4, wherein A is —O—(CH$_2$)$_n$—, wherein n is an integer from 1 to 7.

15. The compound of claim 3, wherein X is O.

16. The compound of claim 4, wherein X is O.

17. The compound of claim 1, which is Compound 18, or a pharmaceutically acceptable salt thereof,

18

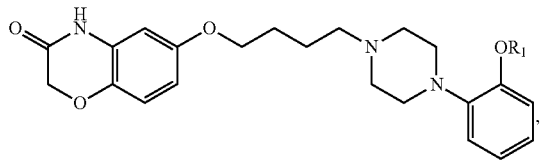

-continued
wherein

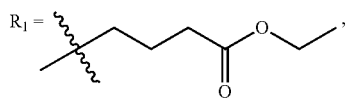
a

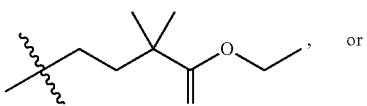
or
b

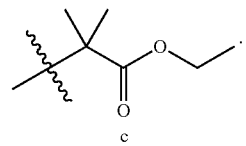
c

18. The compound of claim 4, which is Compound 27, or a pharmaceutically acceptable salt thereof,

27

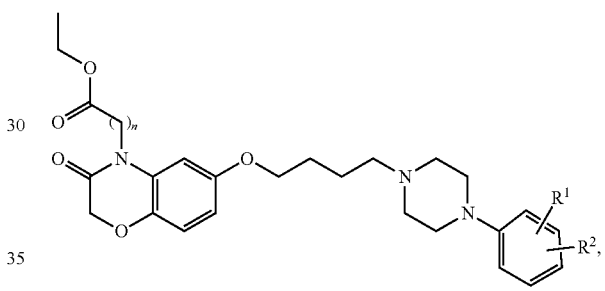

wherein R$^1$ is 2-methoxy or 2-Cl, R$^2$ is H or 3-Cl, and n=1 or 3.

19. A method of treating a patient suffering from psychoses, schizophrenia, acute manic, bipolar disorder, autistic disorder, or depression, comprising;
  administering to a patient in need thereof the compound of claim 1, or racemic mixtures thereof, diasteromeric mixtures thereof, optical isomers thereof, isotopes thereof, or a pharmaceutically acceptable salt thereof.

20. The method of claim 19, wherein the patient suffers from schizophrenia.

21. The method of claim 19, wherein the patient suffers from bipolar disorder.

22. The method according to claim 19, wherein the compound is administered by oral, parenteral, or subcutaneous administration.

23. A method of treating a patient suffering from psychoses, schizophrenia, acute manic, bipolar disorder, autistic disorder, or depression, comprising;
  administering to a patient in need thereof the compound of claim 3, or racemic mixtures thereof, diasteromeric mixtures thereof, optical isomers thereof, isotopes thereof, or a pharmaceutically acceptable salt thereof.

24. The method of claim 23, wherein the patient suffers from schizophrenia.

25. The method of claim 23, wherein the patient suffers from bipolar disorder.

26. The method according to claim 23, wherein the compound is administered by oral, parenteral, or subcutaneous administration.

27. A method of treating a patient suffering from psychoses, schizophrenia, acute manic, bipolar disorder, autistic disorder, or depression, comprising;

administering to a patient in need thereof the compound of claim 4, or racemic mixtures thereof, diasteromeric mixtures thereof, optical isomers thereof, isotopes thereof, or a pharmaceutically acceptable salt thereof.

28. The method of claim 27, wherein the patient suffers from schizophrenia.

29. The method of claim 27, wherein the patient suffers from bipolar disorder.

30. The method according to claim 27, wherein the compound is administered by oral, parenteral, or subcutaneous administration.

* * * * *